United States Patent
Gardai et al.

(10) Patent No.: US 11,202,827 B2
(45) Date of Patent: *Dec. 21, 2021

(54) DOSAGE AND ADMINISTRATION OF NON-FUCOSYLATED ANTI-CD40 ANTIBODIES

(71) Applicant: Seagen Inc., Bothell, WA (US)

(72) Inventors: Shyra Gardai, Bothell, WA (US); Che-Leung Law, Shoreline, WA (US); Stanford Peng, Seattle, WA (US); Jing Yang, Bothell, WA (US); Haley Neff-LaFord, Lake Stevens, WA (US); Thomas John Manley, Seattle, WA (US)

(73) Assignee: Seagen Inc., Bothell, WA (US)

( * ) Notice: Subject to any disclaimer, the term of this patent is extended or adjusted under 35 U.S.C. 154(b) by 347 days.

This patent is subject to a terminal disclaimer.

(21) Appl. No.: 15/411,741

(22) Filed: Jan. 20, 2017

(65) Prior Publication Data

US 2017/0137528 A1    May 18, 2017

Related U.S. Application Data

(63) Continuation-in-part of application No. PCT/US2015/058108, filed on Oct. 29, 2015.

(60) Provisional application No. 62/134,955, filed on Mar. 18, 2015, provisional application No. 62/072,031, filed on Oct. 29, 2014.

(51) Int. Cl.
| | |
|---|---|
| *A61K 39/395* | (2006.01) |
| *C07K 16/28* | (2006.01) |
| *A61M 25/00* | (2006.01) |
| *A61K 39/00* | (2006.01) |

(52) U.S. Cl.
CPC ........ *A61K 39/3955* (2013.01); *A61K 39/395* (2013.01); *A61K 39/39558* (2013.01); *A61M 25/002* (2013.01); *A61M 25/0012* (2013.01); *A61M 25/0017* (2013.01); *C07K 16/2878* (2013.01); *A61K 2039/505* (2013.01); *A61K 2039/507* (2013.01); *A61K 2039/545* (2013.01); *A61M 25/0068* (2013.01); *C07K 2317/24* (2013.01); *C07K 2317/41* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,874,082 A | 2/1999 | De Boer |
| 6,248,516 B1 | 6/2001 | Winter |
| 6,838,261 B1 | 1/2005 | Siegall et al. |
| 6,843,989 B1 | 1/2005 | Siegell et al. |
| 6,946,129 B1 | 9/2005 | Siegell et al. |
| 7,338,660 B2 | 3/2008 | Bedian et al. |
| 7,498,032 B2 | 3/2009 | Siegell et al. |
| 7,510,711 B2 | 3/2009 | Siegell et al. |
| 7,666,422 B2 | 2/2010 | Siegell et al. |
| 7,824,683 B2 | 11/2010 | Siegell et al. |
| 8,303,955 B2 | 11/2012 | Presta et al. |
| 8,492,531 B2 | 7/2013 | Presta et al. |
| 8,551,485 B2 | 10/2013 | Bernett et al. |
| 2002/0031512 A1 | 3/2002 | Pasch et al. |
| 2002/0142358 A1 | 10/2002 | Mikayama et al. |
| 2003/0099644 A1* | 5/2003 | Ahuja ............... C07K 16/2878 424/144.1 |
| 2003/0165499 A1 | 9/2003 | Chu et al. |
| 2003/0211100 A1 | 11/2003 | Bedian et al. |
| 2004/0109857 A1 | 6/2004 | Chu et al. |
| 2004/0120948 A1 | 6/2004 | Mikayama et al. |
| 2008/0199471 A1 | 8/2008 | Bernett et al. |
| 2011/0027276 A1 | 2/2011 | Bernett et al. |
| 2012/0258496 A1 | 10/2012 | Ellwanger et al. |
| 2013/0071403 A1* | 3/2013 | Rolland ........... A61K 39/39558 424/142.1 |
| 2013/0315900 A1 | 11/2013 | Presta et al. |
| 2014/0099254 A1 | 4/2014 | Chang et al. |

FOREIGN PATENT DOCUMENTS

| | | |
|---|---|---|
| WO | WO 1997/031025 | 8/1997 |
| WO | WO 1999/042075 | 8/1999 |
| WO | WO00/75348 A1 | 12/2000 |
| WO | WO2003/040170 A3 | 5/2003 |
| WO | WO 2005/063289 | 7/2005 |
| WO | WO2006/128103 A2 | 11/2006 |
| WO | WO2007/075326 A2 | 7/2007 |
| WO | WO2007/113648 A2 | 10/2007 |
| WO | WO 2009/062125 | 5/2009 |
| WO | 2009/094391 A1 | 7/2009 |
| WO | 2009/135181 A2 | 11/2009 |

OTHER PUBLICATIONS

Rudikoff et al ,Proc Natl Acad Sci USA 79: 1979-1983 (1982). (Year: 1982).*
Colman, Research in Immunology 145: 33-36 (1994). (Year: 1994).*
Kussie et al.,(. Immunol. 152: 146-152 (1994). (Year: 1994).*
Chen et al., EMBO J., 14:2784-2794(1995). (Year: 1995).*
Melero et al., Clin. Cancer Res 15:1507-1509 (2009). (Year: 2009).*
Yamane-Ohnuki et al. (May 2009) "Production of therapeutic antibodies with controlled Fucosylation," MABS, Landes Bioscience, US, vol. 1, No. 3, pp. 230-236.
Mori et al. (Oct. 2007) "Non-fucosylated therapeutic antibodies: the next generation of therapeutic antibodies," Cytotechnology, Kluwer Academic Publishers, DO, vol. 55, No. 2-3, pp. 109-114.
Natsume et al. (Sep. 2009) "Improving effector functions of antibodies for cancer treatment: Enhancing ADCC and CDC Introduction: Current status of therapeutic antibodies," Drug Design, Development and Therapy, 21, pp. 3-7.
Kellner et al. (Jan. 2014) "Boosting ADCC and CDC activity by Fc engineering and evaluation of antibody effector functions," Methods, vol. 65, No. 1, pp. 105-113.

(Continued)

*Primary Examiner* — Phillip Gambel
(74) *Attorney, Agent, or Firm* — Fish & Richardson P.C.

(57) ABSTRACT

This invention relates methods of using a non-fucosylated anti-CD40 antibody for treatment of cancer and chronic infectious diseases.

170 Claims, 25 Drawing Sheets

Specification includes a Sequence Listing.

(56) References Cited

OTHER PUBLICATIONS

Sorensen et al. (Sep. 2010) "Adenoviral vaccination combined with CD40 stimulation and CTLA-4 blockage can lead to complete tumor regression in a murine melanoma model", Vaccine, Elsevier, Amsterdam, NL, vol. 28, No. 41, pp. 6757-6764.
Ferroni et al. (2007) "Contribution of Platelet-Derived CD40 Ligand to Inflammation, Thrombosis and Neoangiogenesis", Curr. Med. Chem., 14, pp. 2170-2180.
Van Kooten et al. (2000) "CD40-CD40 ligand,"J. Leukoc. Biol., 67, pp. 2-17.
Kehry (1996) "CD40-Mediated Signaling in B Cells Balancing Cell Survival, Growth, and Death," J. Immunol., 156, pp. 2345-2348.
Elgueta (2009) "Molecular mechanism and function of CD40/CD40L engagement in the immune system," Immunol. Rev., 229, pp. 152-172.
French et al. (1999) "CD40 antibody evokes a cytotoxic T-cell response that eradicates lymphoma and bypasses T-cell help," Nat. Med., 5, pp. 548-553.
Gajewski et al. (2013) "Innate and adaptive immune cells in the tumor microenvironment," Nat. Immunol., 14, pp. 1014-1022.
Kurts et al. (2010) "Cross-priming in health and disease," Nat. Rev. Immunol., 10, pp. 403-414.
De Vos et al. (2014) "A phase II study of dacetuzumab (SGN-40) in patients with relapsed diffuse large B-cell lymphoma (DLBCL) and correlative analyses of patient-specific factors," J Hematol Oncol., 7, 9 pp.
Paulie et al. (1984) "Monoclonal antibodies to antigens associated with transitional cell carcinoma of the human urinary bladder: Determination of the selectivity of six antibodies by cell ELISA and immunofluorescence," Cancer Immunol. Immunother., 17, pp. 165-179.
Pardoll (2012) "The blockade of immune checkpoints in cancer immunotherapy," Nature Rev. Cancer, 12, pp. 252-264.
Nirschl et al. (2013) "Molecular Pathways: Coexpression of Immune Checkpoint Molecules: Signaling Pathways and Implications for Cancer Immunotherapy," Clin. Cancer Res., 19, pp. 4917-4924
Kroemer et al. (2013) "Immunogenic Cell Death in Cancer Therapy," Annu. Rev. Immunol., 31, pp. 51-72.
Nimmerjahn et al. (2005) "FcγRIV: A Novel FcR with Distinct IgG Subclass Specificity," Immunity, 23, pp. 41-51.
Bruhns (2012) "Properties of mouse and human IgG receptors and their contribution to disease models," Blood, 119, pp. 5640-5649.
Vonderheide et al. (2013) "Phase I study of the CD40 agonist antibody CP-870,893 combined with carboplatin and paclitaxel in patients with advanced solid tumors," OncoImmunology 2:1, e23033, 10 pp.
Advani, et al., "Phase 1 Study of Humanized Anti-CD40 Monoclonal Antobody Dacetuzumab in Refractory or Recurrent Non-Hodgkin's Lymphoma", Journal of Clinical Oncology, vol. 27, No. 26, pp. 4371-4377 (Sep. 2009).
Beatty, et al., "A Phase I Study of an Agonist CD40 Monoclonal Antibody (CP-870,893) in Combination with Gemcitabine in Patients with Advanced Pancreatic Ductal Adenocarcinoma", Clin Cancer Res, 19(22), pp. 6286-6295 (Nov. 2013).
Coveler et al., "SEA-CD40 is a CD40 agonist with early evidence of pharmacodynamic and antitumor activity: preliminary results from a phase I study in advanced solid malignancies", Journal for ImmunoTherapy of Cancer, 4(Suppl 1), p. 145, (2016).
Coveler et al., "SEA-CD40 is a CD40 agonist with early evidence of pharmacodynamic and antitumor activity: preliminary results from a phase I study in advanced solid malignancies", Society for Immunotherapy of Cancer, Annual Meeting, Poster No. 150, 1 page, (2016).
Francisco, et al., "Agonistic Properties and in Vivo Antitumor Activity of the Anti-CD40 Antibody SGN-14", Cancer Research 60, pp. 3225-3231 (Jun. 15, 2000).

Furman, et al., "A phase I study of dacetuzumab (SGN-40, a humanized anti-CD40 monoclonal antibody) in patients with chronic lymphocytic leukemia", Leukemia & Lymphoma, 51(2), pp. 228-235, (Feb. 2010).
Gardai et al., "A sugar engineered non-fucosylated anti-CD40 antibody, SEA-CD40, with enhanced immune stimulatory activity alone and in combination with immune checkpoint inhibitors", Journal of Clinical Oncology, vol. 33, No. 15 (May 20 suppl), 1 page, (2015).
Gardai et al., "A sugar engineered non-fucosylated anti-CD40 antibody, SEA-CD40, with enhanced immune stimulatory activity alone and in combination with immune checkpoint inhibitors", ASCO, Annual Meeting, Abstract No. 3074, 1 page, (2015).
Gardai et al., "SEA-CD40, a Sugar Engineered Non-fucosylated Anti-CD40 Antibody with Improved Immune Activating Capabilities", AACR, Annual Meeting, Abstract No. 2472, 1 page, (2015).
Gardai et al., "SEA-CD40, a Sugar Engineered Non-fucosylated Anti-CD40 Antibody with Improved Immune Activating Capabilities", AACR, Annual Meeting, Abstract No. 2472, 2 pages, Available at: http://www.abstractsonline.com/Plan/AbstractPrintView.aspx?mID=3682&sKey+9e96c326 (2015).
Gardai et al., "SEA-CD40: From Bench to Bedside", AACR, Annual Meeting, Abstract No. 4994, 1 page, (2016).
Gardai et al., "SEA-CD40: From Bench to Bedside", Proceedings of the 107$^{th}$ Annual Meeting of the American Association for Cancer Research, 76(14 Suppl), Abstract No. 4994, 4 pages, (2016).
Gardai et al., "Therapeutic Activity of Effector Function-Enhanced, Non-fucosylated Anti-CD40 Antibodies in Preclinical Immune-Competent Rodent Tumor Models", AACR, Annual Meeting, Abstract No. 4412, 1 page, (2017)
Gardai et al., "Therapeutic activity of effector function-enhanced, non-fucosylated anti-CD40 antibodies in preclinical immune-competent rodent tumor models", Proceedings of the American Association for Cancer Research, vol. 58, #3647, pp. 929-930, (Apr. 2017).
Genentech, Inc., "Highlights of Prescribing Information" Reference ID: 3533989, (2013), Available at: https://www.gene.com/download/pdf/gazyva_prescribing.pdf, 15 pages.
Heath et al., "Monoclonal antibodies to murine CD40 define two distinct functional epitopes", Eur. J. Immunol. 24, pp. 1828-1834, (1994).
Ishida, et al., "Defucosylated Anti-CCR4 Monoclonal Antibody (KW-0761) for Relapsed Adult T-Cell Leukemia-Lymphoma: A Multicenter Phase II Study", Journal of Clinical Oncology, vol. 30, No. 8, pp. 837-842 (Mar. 2012).
Khubchandani, et al., "Dacetuzumab, a humanized mAb against CD40 for the treatment of hematological malignancies", Current Opinion in Investigational Drugs, 10(6), pp. 579-587 (2009).
Lazar, et al., "Engineered antibody Fc variants with enhanced effector function", PNAS, vol. 103, No. 11, pp. 4005-4010 (Mar. 14, 2006).
Lewis, et al., "Distinct Apoptotic Signaling Characteristics of the Anti-CD40 Monoclonal Antibody Dacetuzumab and Rituximab Produce Enhanced Antitumor Activity in Non-Hodgkin Lymphoma", Clin Cancer Res, 17(14), pp. 4672-4681 (Jul. 15, 2011).
Lewis, et al., "Proapoptotic signaling activity of the anti-CD40 monoclonal antibody dacetuzumab circumvents multiple oncogenic transformation events and chemosensitizes NHL cells", Leukemia, pp. 1-10 (2011).
Li, et al., "Inhibitory Fcγ Receptor Engagement Drives Adjuvant and Anti-Tumor Activities of Agonistic CD40 Antibodies", Science, vol. 333, pp. 1030-1034 (Aug. 19, 2011).
Oflazoglu, et al., "Macrophages and Fc-receptor interactions contribute to the antitumor activities of the anti-CD40 antibody SGN-40", British Journal of Cancer 100(1), pp. 113-117, (2009).
Okeley, et al., "Development of orally active inhibitors of protein and cellular fucosylation", PNAS vol. 110, No. 14, pp. 5404-5409 (2013).
PCT Application No. PCT/US2015/058108, Search Report and Written Opinion dated Jan. 12, 2016, 14 pages.
Vonderheide, et al., "Agonistic CD40 Antibodies and Cancer Therapy", Clin Cancer Res 19, pp. 1035-1043 (2013).

(56) References Cited

OTHER PUBLICATIONS

Chen et al., "Enhancement and destruction of antibody function by somatic mutation: unequal occurrence is controlled by V gene combinatorial associations," The EMBO Journal, 14(12):2784-2794, (Year: 1995).
Colman, P. M., "Effects of amino acid sequences changes on antibody-antigen interactions," Research in Immunology, 145:33-36, (Year: 1994).
D'Angelo et al., "Many Routes to an Antibody Heavy-Chain CDR3: Necessary, Yet Insufficient, for Specific Binding," Frontiers in Immunology, vol. 9, Article 395 Mar. 2018; (Year: 2018).
Kussie et al., "A single engineered amino acid substitution changes antibody fine specificity," J. Immunol., 152:146-152, (Year: 1994).
Melero et al., "Palettes of vaccines and immunostimulatory monoclonal antibodies for combination," Clin. Cancer Res., 15:1507-1509, (Year: 2009).
Piche-Nicholas et al., "Changes in complementarity-determining regions significantly alter IgG binding to the neonatal Fc receptor (FcRN) and pharmacokinetics," MABS 2018, vol. 10, No. 1 81-94, (Year: 2018).
Rudikoff et al., "Single amino acid substitution altering antigen-binding specificity," Proc. Natl. Acad. Sci. USA, 1979-1983, (Year: 1982).
Grilley-Olson et al., "SEA-CD40, a non-fucosylated CD40 agonist: Interim results from a phase 1 study in advanced solid tumors," Journal of Clinical Oncology, 2018, 3093, 4 pages, abstract only.
Vonderheide et al., "Agonistic CD40 antibodies and cancer therapy," CCRFocus, 2013, 1033-1043.
Amster, et al., "Synthesis of part of a mouse immunoglobulin light chain in a bacterial clone," Nucl. Acids Res., 1980, 8(19):2055-2065.
Atwell, et al., "Design and expression of a stable bispecific scFv dimer with affinity for both glycophorin and N9 neuraminidase" Molecular Immunology, 1996, 33(17/18):1301-1312.
Boss, et al., "Assembly of functional antibodies from immunoglobulin heavy and light chains synthesised in *E. coli*," Nucl. Acids Res., 1984, 12(9):3791-3806.
Bothwell, et al., "Somatic variants of murine immunoglobulin λ light chains," Nature, 1982, 298:380-382.
Breiner, et al., "Somatic DNA rearrangement generates functional rat immunoglobulin κ chain genes: The jk gene cluster is longer in rat than in mouse," Gene, 1982, 18(2):165-174.
Carter et al., "Engineering antibodies for imaging and therapy," Curr. Opin. Biotechnol., 1997, 8(4):449-454.
Chaudri et al., "Dual specificity antibodies using a double-stranded oligonucleotide bridge," FEBS Letters, 1999, 450(1-2):23-26.
Chothia et al., "Canonical structures for the hypervariable regions of immunoglobulins," J. Mol. Biol., 1987, 196(4):901-917.
Chothia, et al., "Conformations of immunoglobulin hypervariable regions" Nature, 1989, 342:878-883.
Ellison, et al., "Nucleotide sequence of a human immunoglobulin C-gamma-4 gene," DNA, 1981, 1(1):11-18.
Ellison, et al., "The nucleotide sequence of a human immunoglobulin C gammal gene," Nucleic Acids Res., 1982, 10(13):4071-4079.
European Search Report and Opinion in EP Appln. No. 15854895.8, dated May 22, 2018, 9 pages.
GenBank Accession No. J00228, "*Homo sapiens* immunoglobulin gamma-1 heavy chain constant region (IGHG1) gene, partial cds," dated Dec. 2, 1998.
Herbst et al., "Predictive correlates of response to the anti-PD-L1 antibody MPDL3280A in cancer patients," Nature, 2014, 515(7528):563-567.
Hu, et al., "Minibody: a novel engineered anti-carcinoembryonic antigen antibody fragment (single-chain Fv-CH3) which exhibits rapid, high-level targeting of xenografts," Cancer Res., 1996, 56(13):3055-3061.
Karlin, et al., "DNA sequence patterns in human, mouse, and rabbit immunoglobulin kappa-genes," J. Mol. Evol., 1985, 22(3):195-208.

Kenten et al., "Cloning and sequence determination of the gene for the human immunoglobulin epsilon chain expressed in a myeloma cell line," Proc. Natl. Acad. Sci. USA, 1982, 79(21):6661-6665.
Kindsvogel, et al., "A cloned cDNA probe for rat immunoglobulin epsilon heavy chain: construction, identification, and DNA sequence," DNA, 1982, 1(4):335-343.
Kondo, et al., "Signal joint of immunoglobulin Vλ1-Jλ and novel joints of chimeric V pseudogenes on extrachromosomal circular DNA from chicken bursa," Eur. J. Immunol., 1993, 23:245-249.
Lu, et al., "Fab-scFv fusion protein: an efficient approach to production of bispecific antibody fragments," J. Immunol. Methods, 2002, 267(2):213-226.
Lutzky, et al., "A phase 1 study of MEDI4736, an anti-PD-L1 antibody, in patients with advanced solid tumors," J. Clin. Oncol., 2014, 15(Suppl.):3001, DOI: 10.1200/jco.2014.32.15_suppl.3001 (Abstract Only).
Muyldermans et al., "Unique single-domain antigen binding fragments derived from naturally occurring camel heavy-chain antibodies" J. Mol. Recog., 1999, 12:131-140.
Nguyen, et al., "Camel heavy-chain antibodies: diverse germline VHH and specific mechanisms enlarge the antigen-binding repertoire," EMBO J., 2000, 19(5):921-930.
Pack et al., "Miniantibodies: use of amphipathic helixes to produce functional, flexibly linked dimeric FV fragments with high avidity in *Escherichia coli*," Biochem., 1992, 31(6):1579-1584.
Padlan et al., "Anatomy of the antibody molecule," Mol. Immunol., 1994, 31(3):169-217.
Pessi, et al., "A designed metal-binding protein with a novel fold," Nature, 1993, 362:367-369.
Qiu, et al., "Small antibody mimetics comprising two complementarity-determining regions and a framework region for tumor targeting," Nature Biotechnol., 2007, 25:921-929.
Riechmann, et al., "Reshaping human antibodies for therapy," Nature, 1988, 332:323-327.
Rotman, et al., "'DURVIT': a phase-I trial of single low-dose durvalumab (Medi736) intratumourally injected in cervical cancer: safety, toxicity and effect on the primary tumour- and lymph node microenvironment," BMC Cancr, 2018, 18:888.
Rusconi et al., Transmission and expression of a specific pair of rearranged immunoglobulin μ and κ genes in a transgenic mouse line, Nature, 1985, 314:330-334.
Seno, et al., "Molecular cloning and nucleotide sequencing of human immunoglobulin € chain cDNA," Nucl. Acids Res., 1983, 11:719-726, 1983.
Van der Loo, et al., "Characterization and DNA sequence of the b6w2 allotype of the rabbit immunoglobulin kappa 1 light chain (b locus)," Immunogenetics, 1995, 42(5):333-341.
Wang et al., "Antibody Structure, Instability, and Formulation," Journal of Pharmaceutical Sciences, 2007, 96(1):1-26.
Ward, et al., "Binding activities of a repertoire of single immunoglobulin variable domains secreted from *Escherichia coli*," Nature, 1989, 341:544-546.
Zuo, et al., "An efficient route to the production of an IgG-like bispecific antibody," Protein Engineering, 2000, 13:361-367.
Zippelius et al., Induced PD-L1 expression mediates acquired resistance to agonistic anti-CD40 treatment, Cancer Immunol Res. 2015, 9-12, abstract.
Goetze et al., "High-mannose glycans on the Fc region of therapeutic IgG antibodies increase serum clearance in humans," Glycobiology, 2011, 21:949-959.
Li et al., "Inhibitory Fcγ receptor engagement drives adjuvant and antitumor activities of agonistic CD40 antibodies," Science, 2011, 333(6045):1030-1034.
Mayes et al., "The promise and challenges of immune agonist antibody development in cancer," Nature Reviews, 2018, 1-19.
Piechutta et al., "New emerging targets in cancer immunotherapy: the role of Cluster of Differentiation 40 (CD40/TNFR5)," ESMO Open, 2019, 4:e000510.
Stewart et al., "The role of Fc gamma receptors in the activity of immunomodulatory antibodies for cancer," 2014, Journal for ImmunoTherapy of Cancer, 2(29):1-10.

(56) References Cited

OTHER PUBLICATIONS

Thomann et al., "In Vitro Glycoengineering of IgG1 and Its Effect on Fc Receptor Binding and ADCC Activity," PLOS One, 2015, 10(8):e0134949.
Carlson et al., "CD40/CTLA-4 Combo Hits Melanoma in Two Phases of Cancer-Immune Cycle," Oncology Times, 2015, 37(13):36-37.
Storz, Ulrich. "Intellectual property issues of immune checkpoint inhibitors." MAbs. vol. 8. No. 1. Taylor & Francis, 2016.
Five Prime Therapeutics, Inc., "A Study of Bemarituzumab (FPA144) Combined With Modified TOLFOX6(mFOLFOX6) in Gastric/Gastroesophageal Junction Cancer (FIGHT) (FIGHT)," ClinicalTrails.gov., 2018, 1-7.
Five Prime Therapeutics, Inc., "APX005M and Doxorubicin in Advanced Sarcoma)," ClinicalTrails.gov., 2018, 1-9.
Five Prime Therapeutics Inc. "Anti-CCR4 Monoclonal Antibody (Mogamulizumab) and Total Skin Electron BeamTherapy (TSEB) in Patients With Stage IB-IIB Cutaneous T-Cell Lymphoma (MOGAT)," ClincalTrials.gov., 2019, 1-11 pages.
Five Prime Therapeutics Inc. "A Safety Study in Patients With Chronic Lymphocytic Leukemia," ClinicalTrials.gov., 2006, 1-8 pages.
Five Prime Therapeutics Inc. "Study of SGN-40 in Patients With Relapsed Diffuse Large B-Cell Lymphoma" ClincalTrials.gov., 2007, 1-7 pages.
Five Prime Therapeutics Inc. "A Phase 2, Multicenter, Randomized, Open-label Study of MEDI-551 in Adults WithRelapsed or Refractory Diffuse Large B-Cell Lymphoma (DLBCL)a" ClinicalTrials.gov., 2018, 1-13 pages.
Five Prime Therapeutics Inc. "An Expanded Access, Open-Label Study of Obinutuzumab (GA101) PlusChlorambucil in Patients With Previously Untreated Chronic Lymphocytic Leukemia" ClincalTrials.gov., 2016, 1-7 pages.
Five Prime Therapeutics Inc. "Trial ofKB004 in Patients With Glioblastoma" ClincalTrials.gov., 201, 1-8 pages.
Five Prime Therapeutics Inc. "A Study of Safety, Pharmacokinetics and Pharmacodynamics of JNJ-64457107 inParticipants With Advanced Stage Tumors" ClincalTrials.gov., 2016, 1-8 pages.
Vonderheide et al., Phase I Study of Recombinant Human CD40 Ligand in Cancer Patients, Journal of Clinical Oncology, 2001, 19(13):3280-3287.
Advani et al., "A Phase 2 Clinical Trial of SGN-40 (Dacetuzumab) Monotherapy in Relapsed Diffuse Large B-Cell Lymphoma", 50th ASH Annual Meeting, Dec. 2008, Abstract No. 1000, 1 pages.
Advani et al., "A Phase 2 Clinical Trial of SGN-40 Monotherapy in Relapsed Diffuse Large B-Cell Lymphoma", Biologic Therapies for NHL (Excluding Pre-clinical Models) Poster I, Dec. 2008, 1 pages.
ClinicalTrials.gov [online], "History of Changes for Study: NCT02376699: Safety Study of SEA-CD40 in Cancer Patients", U.S. National Libraiy of Medicine, Dec. 21, 2018, 9 pages.
ClinicalTrials.gov [online], "History of Changes for Study: NCT02376699: Safety Study of SEA-CD40 in Cancer Patients", U.S. National Library of Medicine, Feb. 25, 2015, 5 pages.
ClinicalTrials.gov [online], "History of Changes for Study: NCT02376699: Safety Study of SEA-CD40 in Cancer Patients", U.S. National Library of Medicine, Jan. 23, 2017, 7 pages.
ClinicalTrials.gov [online], "History of Changes for Study: NCT02376699: Safety Study of SEA-CD40 in Cancer Patients", U.S. National Library of Medicine, Mar. 12, 2021, 9 pages.
ClinicalTrials.gov [online], "History of Changes for Study: NCT02376699: Safety Study of SEA-CD40 in Cancer Patients", U.S. National Library of Medicine, Nov. 30, 2015, 6 pages.
ClinicalTrials.gov [online], "History of Changes for Study: NCT02376699: Safety Study of SEA-CD40 in Cancer Patients", U.S. National Library of Medicine, Nov. 30, 2016, 7 pages.
ClinicalTrials.gov [online], "History of Changes for Study: NCT02376699: Safety Study of SEA-CD40 in Cancer Patients", U.S. National Library of Medicine, Oct. 28, 2015, 6 pages.
ClinicalTrials.gov [online], "History of Changes for Study: NCT02376699: Safety Study of SEA-CD40 in Cancer Patients", U.S. National Library of Medicine, Sep. 6, 2019, 10 pages.
ClinicalTrials.gov [online], "NCT:02376699: Safety Study of SEA-CD40 in Cancer Patients", U.S. National Libraiy of Medicine, Mar. 3, 2015, 11 pages.
EP Extended European Search Report in European Appln. No. 20212733.8, dated May 11, 2021, 11 pages.
Kelley et al., "Preclinical pharmacokinetics, pharmacodynamics, and activity of a humanized anti-CD40 antibody (SGN-40) in rodents and non-human primates", British Journal of Pharmacology, 2006, 148:1116-1123.
PCT International Preliminary Report on Patentability in International Appln. No. PCT/US2015/058108, dated May 11, 2017, 9 pages.
Polo et al., "Reversible disruption of BCL6 repression complexes by CD40 signaling in normal and malignant B cells", Blood, May 2008, 112: 644-651.
Tai et al., "Immunomodulatory Drug Lenalidomide (CC-5013, IMiD3) Augments Anti-CD40 SGN•4Q-lnduced Cytotoxicity in Human Multiple Myeloma: Clinical Implications", Cancer Research, Dec. 2005, 65(24): 11712-11720.
Tai et al., "Mechanisms by which SGN-40, a Humanized Anti-CD40 Antibody, Induces Cytotoxicity in Human Multiple Myeloma Cells: Clinical Implications", Cancer Research, Apr. 2004, 64:2846-2852.
U.S. Appl. No. 15/522,614, filed Oct. 29, 2015, Shyra Jane Gardai, US20170333556A1, Nov. 23, 2017, Shyra Jane Gardai.
U.S. Appl. No. 15/411,741, filed Jan. 20, 2017, Shyra Jane Gardai, US20170137528A1, May 18, 2017, Shyra Jane Gardai.

* cited by examiner

2A

2B.

| | | |
|---|---|---|
| FcγRIIIa (158F) | 27.5 nM | 302.7nM |
| FcγRIIIa (158V) | 5.2 nM | 37.9nM |

4A

4B

5A

5B

10A

10B

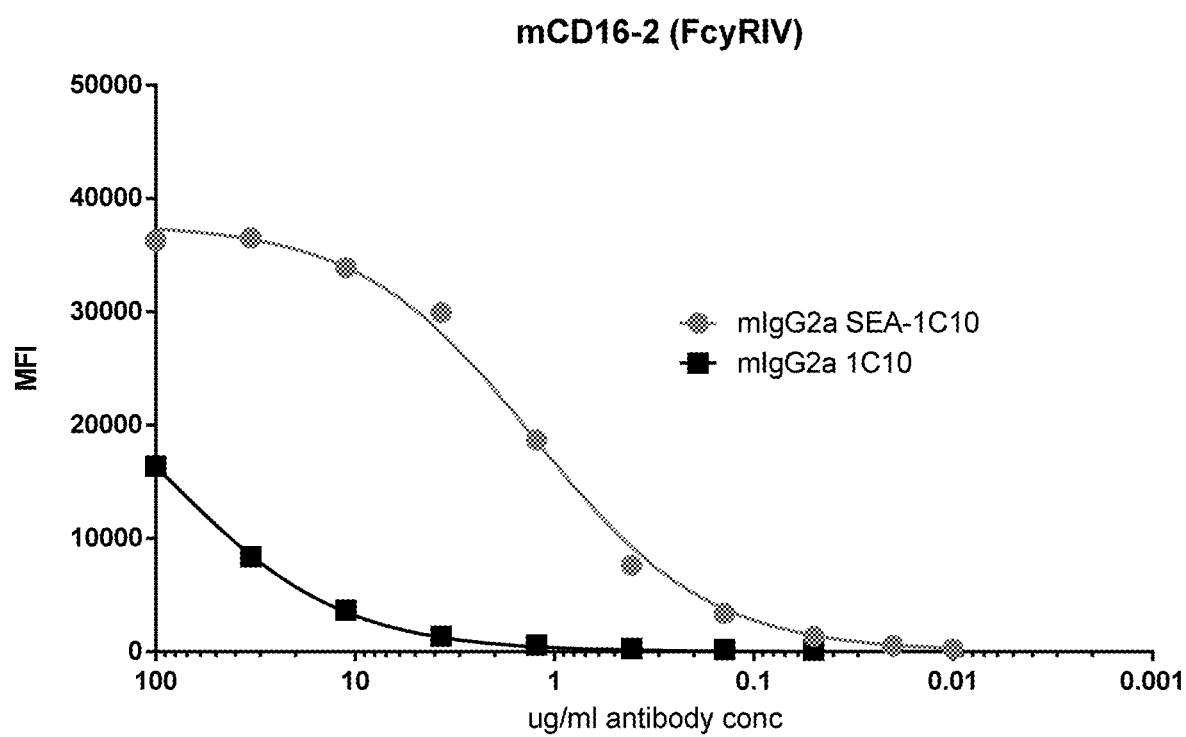

SEQUENCE LISTING

<160> NUMBER OF SEQ ID NOS: 2

<210> SEQ ID NO 1
<211> LENGTH: 444
<212> TYPE: PRT
<213> ORGANISM: Artificial
<220> FEATURE:
<223> OTHER INFORMATION: hS2C6 heavy chain

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Ala Gly Gly Thr Ser Tyr Asn Gln Lys Phe
    50                  55                  60

Lys Gly Arg Phe Thr Leu Ser Val Asp Asn Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr Cys Pro
            210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440
```

<210> SEQ ID NO 2
<211> LENGTH: 219
<212> TYPE: PRT
<213> ORGANISM: Artificial
<220> FEATURE:
<223> OTHER INFORMATION: hS2C6 light chain

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65              70                  75                  80

Ser Ser Leu Gln Pro Glu Asp Phe Ala Thr Tyr Phe Cys Ser Gln Thr
            85                  90                  95

Thr His Val Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

DOSAGE AND ADMINISTRATION OF NON-FUCOSYLATED ANTI-CD40 ANTIBODIES

CROSS-REFERENCES TO RELATED APPLICATIONS

This application is a continuation-in-part of International Application No. PCT/US2015/058108, filed Oct. 29, 2015 which claims the benefit of U.S. Provisional Application No. 62/072,031, filed on Oct. 29, 2014 and U.S. Provisional Application No. 62/134,955, filed on Mar. 18, 2015; all of which are herein incorporated by reference for all purposes.

FIELD OF THE INVENTION

This disclosure relates methods of using a non-fucosylated anti-CD40 antibody for treatment of cancer and chronic infectious diseases.

BACKGROUND OF THE INVENTION

CD40 is a member of the tumor necrosis factor (TNF) receptor superfamily. It is a single chain type I transmembrane protein with an apparent MW of 50 kDa. CD40 is expressed by some cancer cells, e.g., lymphoma cells and several types of solid tumor cells. CD40 also functions to activate the immune system by facilitating contact-dependent reciprocal interaction between antigen-presenting cells and T cells. Although a number of anti-CD40 antibodies have been tested in clinical trials, to date none have exhibited sufficient activity. The present disclosure solves this and other problems.

BRIEF SUMMARY OF THE INVENTION

This disclosure provides a method of treating cancer, by administering an anti-CD40 antibody to a patient in need of such treatment. The anti-CD40 antibody comprises the heavy chain variable region of SEQ ID NO:1 and the light chain variable region of SEQ ID NO:2, and a human constant region. The constant region has an N-glycoside-linked sugar chain at residue N297 according to the EU index as set forth in Kabat and less than 5% of the N-glycoside-linked sugar chains include a fucose residue, i.e., a fucose bound to the reducing terminal of the sugar chain via an α1,6 bond to N-acetylglucosamine ("GlcNAc"). Administration of the anti-CD40 antibody is at a dose level between 0.1-300 μg/kg (μg antibody per kilogram patient body weight). In one embodiment, the anti-CD40 antibody dose level is between 0.6-150 μg/kg. In another embodiment, the anti-CD40 antibody dose level is between 1.0-100 μg/kg. In another embodiment, the anti-CD40 antibody dose level is between 5-25 μg/kg. In another embodiment, the anti-CD40 antibody dose level is between 8-12 μg/kg. In another embodiment, the anti-CD40 antibody dose level is about 10 μg/kg. In another embodiment, the anti-CD40 antibody the dose level is 10 μg/kg.

In another aspect, this disclosure provides a method of treating cancer, by administering an anti-CD40 antibody to a patient in need of such treatment. The anti-CD40 antibody comprises the heavy chain variable region of SEQ ID NO:1 and the light chain variable region of SEQ ID NO:2, and a human constant region. The constant region has an N-glycoside-linked sugar chain at residue N297 according to the EU index as set forth in Kabat and less than 5% of the N-glycoside-linked sugar chains include a fucose residue, i.e., a fucose bound to the reducing terminal of the sugar chain via an α1,6 bond to N-acetylglucosamine ("GlcNAc"). Administration of the anti-CD40 antibody is at a dose level between 0.1-2000 μg/kg (μg antibody per kilogram patient body weight). In one embodiment, the dose level is between 10-1000 μg/kg. In another embodiment, the dose level is between 50-800 μg/kg. In a further embodiment, the dose level is between 75-600 μg/kg. In another embodiment, the dose level is between 100-500 μg/kg. in further embodiments, the dose level is a range selected from the following: 100-300 μg/kg, 300-500 μg/kg, 500-700 μg/kg, 700-900 μg/kg, and 900-1100 μg/kg. In other embodiments, the dose level is a range selected from the following: 100-150 μg/kg, 150-200 μg/kg, 200-250 μg/kg, 250-300 μg/kg, 300-350 μg/kg, 350-400 μg/kg, 400-450 μg/kg, 450-500 μg/kg, 500-550 μg/kg, 550-600 μg/kg, 600-650 μg/kg, 650-700 μg/kg, 700-750 μg/kg, 750-800 μg/kg, 800-850 μg/kg, 850-900 μg/kg, 900-950 μg/kg, 950-1000 μg/kg, 1000-1050 μg/kg, and 1050-1100 μg/kg. In further embodiments, the dose level is selected from the following: about 60 μg/kg, about 100 μg/kg, about 150 μg/kg, about 200 μg/kg, about 250 μg/kg, about 300 μg/kg, about 350 μg/kg, about 400 μg/kg, about 450 μg/kg, about 500 μg/kg, about 550 μg/kg, about 600 μg/kg, about 650 μg/kg, about 700 μg/kg, about 750 μg/kg, about 800 μg/kg, about 850 μg/kg, about 900 μg/kg, about 950 μg/kg, about 1000-1050 μg/kg, about 1050 μg/kg, and 1110 μg/kg.

In one embodiment, the anti-CD40 antibody is administered every three weeks. In another embodiment the anti-CD40 antibody is administered every six weeks. In another embodiment the anti-CD40 antibody is administered every ten weeks. In another embodiment the anti-CD40 antibody is administered every twelve weeks. In another embodiment the anti-CD40 antibody is administered every fifteen weeks. In another embodiment the anti-CD40 antibody is administered every eighteen weeks.

In another embodiment, the patient has a CD40 positive cancer. In another embodiment, the patient has a CD40 negative cancer. In a further embodiment, the patient has a cancer that is a solid tumor. In yet another embodiment, the patient has a cancer that is a blood cancer. In another embodiment, the cancer is a melanoma, a breast cancer, including metastatic breast cancer, a lung cancer, including a non-small cell lung cancer, or pancreatic cancer.

In one embodiment, this disclosure provides a method of treating cancer, by administering an anti-CD40 antibody to a patient in need of such treatment. The anti-CD40 antibody comprises the heavy chain variable region of SEQ ID NO:1 and the light chain variable region of SEQ ID NO:2, and a human constant region. The constant region has an N-glycoside-linked sugar chain at residue N297 according to the EU index as set forth in Kabat and less than 5% of the N-glycoside-linked sugar chains include a fucose residue, i.e., a fucose bound to the reducing terminal of the sugar chain via an α1,6 bond to N-acetylglucosamine ("GlcNAc"). Administration of the anti-CD40 antibody is at a dose level 30 μg/kg (μg antibody per kilogram patient body weight). In another embodiment, the patient has a CD40 positive cancer. In another embodiment, the patient has a CD40 negative cancer. In a further embodiment, the patient has a cancer that is a solid tumor. In yet another embodiment, the patient has a cancer that is a blood cancer. In another embodiment, the cancer is a melanoma, a breast cancer, including metastatic breast cancer, a lung cancer, including a non-small cell lung cancer, or pancreatic cancer.

In a further aspect, this disclosure provides methods of treating cancer by administering to the patient a combination of the anti-CD40 antibody and an antibody that blocks an immune checkpoint. One example of an antibody that blocks an immune checkpoint is an anti-cytotoxic T-lymphocyte-associated protein 4 (CTLA4) antibody. Examples of anti-CTLA4 antibodies include, e.g., ipilimumab or tremelimumab. Another example of an antibody that blocks an immune checkpoint is an anti-programmed cell death protein 1 (PD1) antibody. Examples of anti-PD1 antibodies include, e.g., nivolumab, pidilizumab, or pembrolizumab. A further example of an antibody that blocks an immune checkpoint is an anti-programmed death-ligand (PD-L1) antibody. Examples of anti-PD-L1 antibodies include, e.g., MEDI4736 and MPDL3280A.

In another embodiment, the patient has a CD40 positive cancer and is treated with a combination of the anti-CD40 antibody and an antibody that blocks an immune checkpoint, e.g., an anti-CTLA4 antibody, an anti-PD1 antibody, or an anti-PD-L1 antibody. In another embodiment, the patient has a CD40 negative cancer and is treated with a combination of the anti-CD40 antibody and an antibody that blocks an immune checkpoint, e.g., an anti-CTLA4 antibody, an anti-PD1 antibody, or an anti-PD-L1 antibody. In a further embodiment, the patient has a cancer that is a solid tumor and is treated with a combination of the anti-CD40 antibody and an antibody that blocks an immune checkpoint, e.g., an anti-CTLA4 antibody, an anti-PD1 antibody, or an anti-PD-L1 antibody. In yet another embodiment, the patient has a cancer that is a blood cancer and is treated with a combination of the anti-CD40 antibody and an antibody that blocks an immune checkpoint, e.g., an anti-CTLA4 antibody, an anti-PD1 antibody, or an anti-PD-L1 antibody. In another embodiment, the cancer is a melanoma, a breast cancer, including metastatic breast cancer, a lung cancer, including a non-small cell lung cancer, or pancreatic cancer, and is treated with a combination of the anti-CD40 antibody and an antibody that blocks an immune checkpoint, e.g., an anti-CTLA4 antibody, an anti-PD1 antibody, or an anti-PD-L1 antibody.

Definitions

A "polypeptide" or "polypeptide chain" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "antibody" is used herein to denote immunoglobulin proteins produced by the body in response to the presence of an antigen and that bind to the antigen, as well as antigen-binding fragments and engineered variants thereof. Hence, the term "antibody" includes, for example, intact monoclonal antibodies comprising full-length immunoglobulin heavy and light chains (e.g., antibodies produced using hybridoma technology) and antigen-binding antibody fragments, such as F(ab')$_2$ and Fab fragments. Genetically engineered intact antibodies and fragments, such as chimeric antibodies, humanized antibodies, single-chain Fv fragments, single-chain antibodies, diabodies, minibodies, linear antibodies, multivalent or multispecific (e.g., bispecific) hybrid antibodies, and the like are also included. Thus, the term "antibody" is used expansively to include any protein that comprises an antigen-binding site of an antibody and is capable of specifically binding to its antigen.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362: 367-369, 1993; Qiu et al., *Nature Biotechnol.* 25:921-929, 2007). More commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, *Biochem.* 31:1579-1584, 1992), a non-peptide linker, an oligonucleotide (see Chaudri et al., *FEBS Letters* 450:23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')$_2$, F(ab)$_c$, diabodies, dAbs, minibodies, nanobodies, Fab-scFv fusions, bispecific (scFv)$_4$-IgG, and bispecific (scFv)$_2$-Fab. (See, e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

As used herein, the term "immunoglobulin" refers to a protein consisting of one or more polypeptides substantially encoded by immunoglobulin gene(s). One form of immunoglobulin constitutes the basic structural unit of native (i.e., natural) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE)

have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function, see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

Full-length immunoglobulin "light chains" (about 25 Kd or 214 amino acids) are encoded by a variable region gene at the amino-terminus (encoding about 110 amino acids) and a by a kappa or lambda constant region gene at the carboxyl-terminus. Full-length immunoglobulin "heavy chains" (about 50 Kd or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally *Fundamental Immunology* (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three hypervariable regions, also called "complementarity determining regions" or "CDRs." The framework regions serve to align the CDRs for specific binding to an epitope of an antigen. Thus, the term "hypervariable region" or "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917, 1987; Chothia et al., *Nature* 342:878-883, 1989. Kabat also provides a widely used numbering convention (Kabat numbering) in which corresponding residues between different heavy chains or between different light chains are assigned the same number. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

Unless the context dictates otherwise, the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The term "chimeric antibody" refers to an antibody having variable domains derived from a first species and constant regions derived from a second species. Chimeric immunoglobulins or antibodies can be constructed, for example by genetic engineering, from immunoglobulin gene segments belonging to different species. The term "humanized antibody," as defined infra, is not intended to encompass chimeric antibodies. Although humanized antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "humanized VH domain" or "humanized VL domain" refers to an immunoglobulin VH or VL domain comprising some or all CDRs entirely or substantially from a non-human donor immunoglobulin (e.g., a mouse or rat) and variable region framework sequences entirely or substantially from human immunoglobulin sequences. The non-human immunoglobulin providing the CDRs is called the "donor" and the human immunoglobulin providing the framework is called the "acceptor." In some instances, humanized antibodies may retain non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain. Immunoglobulin constant region(s) need not be present, but if they are, they are entirely or substantially from human immunoglobulin constant regions.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

With regard to proteins as described herein, reference to amino acid residues corresponding to those specified by SEQ ID NO includes post-translational modifications of such residues.

The term "diluent" as used herein refers to a solution suitable for altering or achieving an exemplary or appropriate concentration or concentrations as described herein.

The term "container" refers to something into which an object or liquid can be placed or contained, e.g., for storage (for example, a holder, receptacle, vessel, or the like).

The term "administration route" includes art-recognized administration routes for delivering a therapeutic protein such as, for example, parenterally, intravenously, intramuscularly, or subcutaneously. For administration of an antibody for the treatment of cancer, administration into the systemic circulation by intravenous or subcutaneous administration may be desired. For treatment of a cancer characterized by a solid tumor, administration can also be localized directly into the tumor, if so desired.

The term "treatment" refers to the administration of a therapeutic agent to a patient, who has a disease with the purpose to cure, heal, alleviate, delay, relieve, alter, remedy, ameliorate, improve or affect the disease.

The term "patient" includes human and other mammalian subjects that receive either prophylactic or therapeutic treatment.

The term "effective amount," "effective dose," or "effective dosage" refers to an amount that is sufficient to achieve or at least partially achieve the desired effect, e.g., sufficient to inhibit the occurrence or ameliorate one or more symptoms of a disease or disorder. An effective amount of a pharmaceutical composition is administered in an "effective regime." The term "effective regime" refers to a combination of amount of the composition being administered and dosage frequency adequate to accomplish prophylactic or therapeutic treatment of the disease or disorder.

As used herein, the term "about" denotes an approximate range of plus or minus 10% from a specified value. For instance, the language "about 20 µg/Kg" encompasses a range of 18-22 µg/Kg. As used herein, about also includes the exact amount. Hence "about 20 µg/Kg" means "about 20 µg/Kg" and also "20 µg/Kg."

BRIEF DESCRIPTION OF THE DRAWINGS

FIG. 2A provides a graphical representation and FIG. 2B provides $K_D$ values. SEA-CD40 values are shown in the left column; decetuzumab values are shown in the right column.

FIG. 4A shows production of tumor necrosis factor-α and FIG. 4B shows production of MIP-1β.

FIG. 5A shows production of tumor necrosis factor-α (TNF-α) and FIG. 5B shows production of MIP-1β.

FIG. 10A shows levels percentages of antigen specific T-cells; FIG. 10B shows levels of IFN-γ production.

FIGS. 15A and 15B demonstrate the binding of fucosylated and non-fucosylated anti-mouse CD40 antibodies to murine Fcγ receptors. Fcγ receptor were either FcγRI (FIG. 15A) or FcγRIV (FIG. 15B).

DETAILED DESCRIPTION

Figure 1:
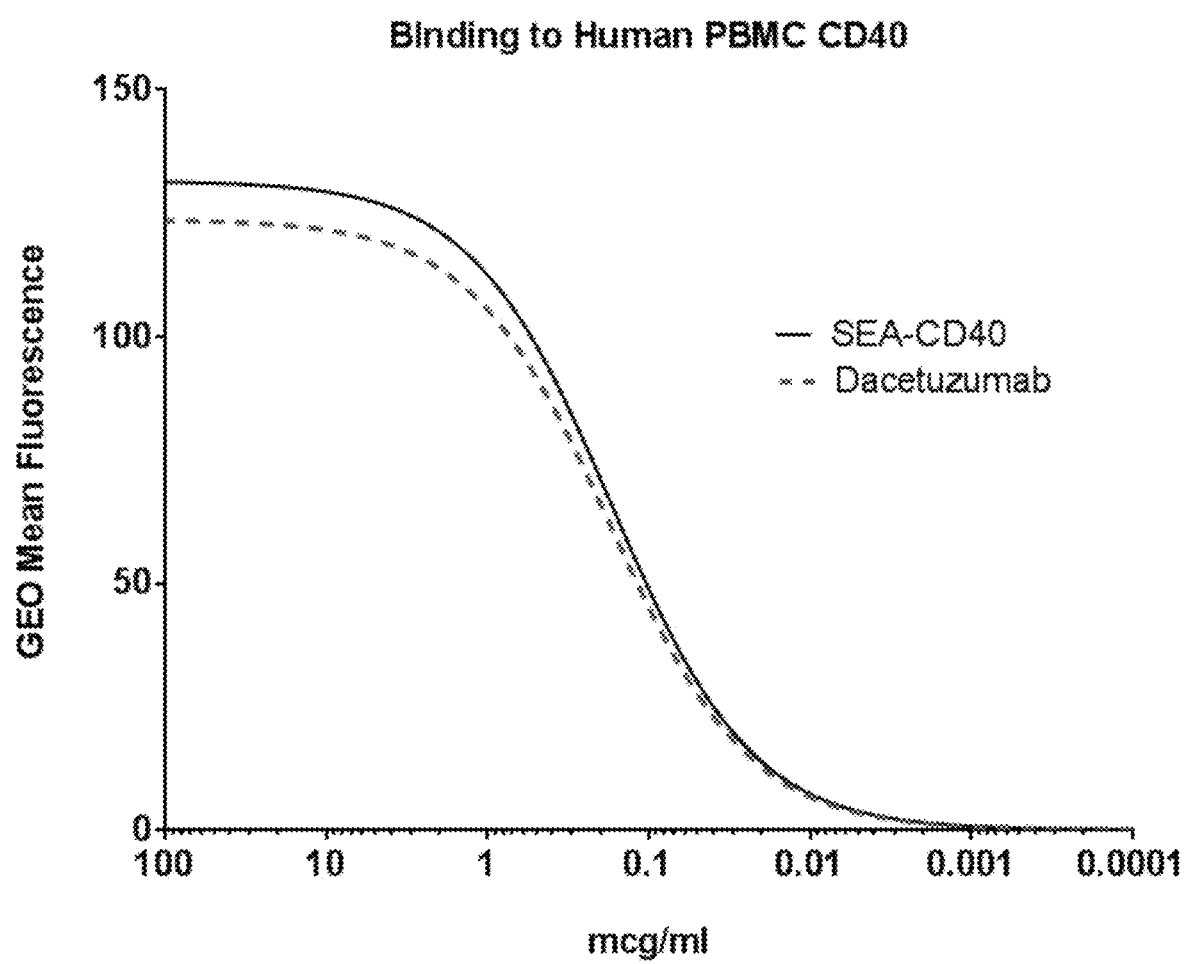
FIG. 1 provides the binding of SEA-CD40 (solid line) and dacetuzumab (dashed line) for the human CD40 protein present on the surface of PBMCs.

This disclosure provides description of the activity of a non-fucosylated anti-CD40 antibody, SEA-CD40. SEA- CD40 is an agonistic antibody and has enhanced binding to Fcγ receptors III and, surprisingly exhibits enhanced activation of the CD40 signaling pathway. Because of its enhanced activation of the CD40 pathway SEA-CD40 is a potent activator of the immune system and can be used to treat cancer or to treat infectious diseases, particularly chronic viral diseases, such as hepatitis C, human immunodeficiency virus, Epstein-Barr virus, cytomegalovirus, John Cunningham virus, and human papilloma virus. Other infectious diseases, include, e.g., tuberculosis. The enhanced activation of the immune system allows SEA-CD40 to be dosed at low levels, as compared to a fucosylated parent antibody.

CD40 Description and Function.

CD40 is a member of the tumor necrosis factor (TNF) receptor superfamily. It is a single chain type I transmembrane protein with an apparent MW of 50 kDa. Its mature polypeptide core consists of 237 amino acids, of which 173 amino acids comprise an extracellular domain (ECD) organized into 4 cysteine-rich repeats that are characteristic of TNF receptor family members. Two potential N-linked glycosylation sites are present in the membrane proximal region of the ECD, while potential O-linked glycosylation sites are absent. A 22 amino acid transmembrane domain connects the ECD with the 42 amino acid cytoplasmic tail of CD40. Sequence motifs involved in CD40-mediated signal transduction have been identified in the CD40 cytoplasmic tail. These motifs interact with cytoplasmic factors called TNF-R-associated factors (TRAFs) to trigger multiple downstream events including activation of MAP kinases and NFκB, which in turn modulate the transcriptional activities of a variety of inflammation-, survival-, and growth-related genes. See, e.g., van Kooten and Bancherau, *J. Leukoc. Biol.* 67:2-17 (2000); Elgueta et al., *Immunol. Rev.* 229:152-172 (2009).

Within the hematopoietic system, CD40 can be found on B cells at multiple stages of differentiation, monocytes, macrophages, platelets, follicular dendritic cells, dendritic cells (DC), eosinophils, and activated T cells. In normal non-hematopoietic tissues, CD40 has been detected on renal epithelial cells, keratinocytes, fibroblasts of synovial membrane and dermal origins, and activated endothelium. A soluble version of CD40 is released from CD40-expressing cells, possibly through differential splicing of the primary transcript or limited proteolysis by the metalloproteinase TNFα converting enzyme. Shed CD40 can potentially modify immune responses by interfering with the CD40/CD40L interaction. See, e.g., van Kooten and Bancherau, *J. Leukoc. Biol.* 67:2-17 (2000); Elgueta et al., *Immunol. Rev.* 229:152-172 (2009).

The endogenous ligand for CD40 (CD40L) is a type II membrane glycoprotein of 39 kDa also known as CD154. CD40L is a member of the TNF superfamily and is expressed as a trimer on the cell surface. CD40L is transiently expressed on activated CD4+, CD8+, and γδ T cells. CD40L is also detected at variable levels on purified monocytes, activated B cells, epithelial and vascular endothelial cells, smooth muscle cells, and DCs, but the functional relevance of CD40L expression on these cell types has not been clearly defined (van Kooten 2000; Elgueta 2009). However, expression of CD40L on activated platelets has been implicated in the pathogenesis of thrombotic diseases. See, e.g., Ferroni et al., *Curr. Med. Chem.* 14:2170-2180 (2007).

The best-characterized function of the CD40/CD40L interaction is its role in contact-dependent reciprocal interaction between antigen-presenting cells and T cells. See, e.g., van Kooten and Bancherau, *J. Leukoc. Biol.* 67:2-17 (2000); Elgueta et al., *Immunol. Rev.* 229:152-172 (2009). Binding of CD40L on activated T cells to CD40 on antigen-activated B cells not only drives rapid B cell expansion, but also provides an essential signal for B cells to differentiate into either memory B cells or plasma cells. CD40 signaling is responsible for the formation of germinal centers in which B cells undergo affinity maturation and isotype switching to acquire the ability to produce high affinity antibodies of the IgG, IgA, and IgE isotypes. See, e.g., Kehry, *J. Immunol.* 156:2345-2348 (1996). Thus, individuals with mutations in the CD40L locus that prevent functional CD40/CD40L interaction suffer from the primary immunodeficiency X-linked hyper-IgM syndrome that is characterized by over-representation of circulating IgM and the inability to produce IgG, IgA, and IgE. These patients demonstrate suppressed secondary humoral immune responses, increased susceptibility to recurrent pyrogenic infections, and a higher frequency of carcinomas and lymphomas. Gene knockout experiments in mice to inactivate either CD40 or CD40L locus reproduce the major defects seen in X-linked hyper-IgM patients. These KO mice also show impaired antigen-specific T cell priming, suggesting that the CD40L/CD40 interaction is also a critical factor for mounting cell-mediated immune responses. See, e.g., Elgueta et al., *Immunol. Rev.* 229:152-172 (2009).

The immune-stimulatory effects of CD40 ligation by CD40L or anti-CD40 in vivo have correlated with immune responses against syngeneic tumors. See, e.g., French et al., *Nat. Med.* 5:548-553 (1999). A deficient immune response against tumor cells may result from a combination of factors such as expression of immune checkpoint molecules, such as PD-1 or CTLA-4, decreased expression of MHC antigens, poor expression of tumor-associated antigens, appropriate adhesion, or co-stimulatory molecules, and the production of immunosuppressive proteins like TGFβ by the tumor cells. CD40 ligation on antigen presenting and transformed cells results in up-regulation of adhesion proteins (e.g., CD54), co-stimulatory molecules (e.g., CD86) and MHC antigens, as well as inflammatory cytokine secretion, thereby potentially inducing and/or enhancing the antitumor immune response, as well as the immunogenicity of the tumor cells. See, e.g., Gajewski et al., *Nat. Immunol.* 14:1014-1022 (2013).

A primary consequence of CD40 cross-linking is DC activation (often termed licensing) and potentiation of myeloid and B cells ability to process and present tumor-associated antigens to T cells. Besides having a direct ability to activate the innate immune response, a unique consequence of CD40 signaling is APC presentation of tumor-derived antigens to CD8+ cytotoxic T cell (CTL) precursors in a process known as 'cross-priming'. This CD40-dependent activation and differentiation of CTL precursors by mature DCs into tumor-specific effectors CTLs may enhance cell-mediated immune responses against tumor cells. See, e.g., Kurts et al., *Nat. Rev. Immunol.* 10:403-414 (2010).

Agonistic CD40 mAbs including dacetuzumab, the SEA-CD40 parent molecule, have shown encouraging clinical activity in single-agent and combination chemotherapy settings. Dacetuzumab demonstrated some clinical activity in a phase 1 study in NHL and a phase 2 study in diffuse large B-cell lymphoma (DLBCL). See, e.g., Advani et al., *J. Clin. Oncol.* 27:4371-4377 (2009) and De Vos et al., *J. Hematol. Oncol.* 7:1-9 (2014). Additionally CP-870,893, a humanized IgG2 agonist antibody to CD40, showed encouraging activity in solid tumor indications when combined with paclitaxel or carboplatin or gemcitabine. In these studies, activation of antigen presenting cells, cytokine production, and generation of antigen-specific T cells were seen. See, e.g., Beatty et al., *Clin. Cancer Res.* 19:6286-6295 (2013) and Vonderheide et al., *Oncoimmunology* 2:e23033 (2013).

Anti-CD40 Antibodies

Because of its role in immune function, antibodies have been raised against the CD40 antigen. Such antibodies can be classified into three groups, antagonistic antibodies, which inhibit CD40 activity; partially agonistic antibodies, which partially induce CD40 activity; and fully agonistic antibodies, which fully stimulate CD40 activity. Members of each of the groups have been tested in clinical trials; none have been approved to date.

SEA-CD40

This disclosure provides a non-fucosylated hS2C6 antibody, SEA-CD40. S2C6 was originally isolated as a murine monoclonal antibody raised against a human bladder carcinoma referred to herein as mS2C6. See, e.g., Paulie et al., *Cancer Immunol. Immunother.* 17:165-179 (1984). The S2C6 antibody is a partial agonist of the CD40 signaling pathway and thus has the following activities: binding to human CD40 protein, binding to cynomologos CD40 protein, activation of the CD40 signaling pathway, potentiation of the interaction of CD40 with its ligand, CD40L. See, e.g., U.S. Pat. No. 6,946,129.

As a next step in development, S2C6 was humanized and this humanized antibody is referred to as humanized S2C6, herein, and alternatively as dacetuzumab, or fucosylated, humanized S2C6 (fhS2C6), or SGN-40. See, e.g., WO 2006/128103. SGN-40 was tested in human clinical trials and was found not to be sufficiently active to warrant further development.

SEA-CD40 is a non-fucosylated humanized S2C6 antibody. The amino acid sequences of the heavy and light chain for SEA-CD40 are disclosed as SEQ ID NO:1 and 2, respectively. The variable region of the heavy chain is from amino acids 1-113 of SEQ ID NO:1; the variable region of the light chain is from amino acids 1-113 of SEQ ID NO:2. The generation of the antibody backbone of SEA-CD40 is disclosed at WO 2006/128103, which is herein incorporated by reference.

This disclosure provides a non-fucosylated, humanized S2C6 antibody, referred to herein as of hS2C6 or SEA-CD40. In addition to enhanced binding to Fc receptors, SEA-CD40 also enhances activity of the CD40 pathway, as compared to the parent antibody, dacetuzumab. The SEA-CD40 antibody thus, is administered to patients at at lower doses and using different schedules of administration.

Non-Fucosylated Antibodies

SEA-CD40 is a non-fucosylated antibody and exhibits enhanced binding to FcγIII receptors, and surprisingly enhanced ability to activate the CD40 signaling pathway in immune cells.

Methods of Making Non Fucosylated Antibodies

This disclosure provides compositions and methods for preparing humanized S2C6 antibodies with reduced core fucosylation. As used herein, "core fucosylation" refers to addition of fucose ("fucosylation") to N-acetylglucosamine ("GlcNAc") at the reducing terminal of an N-linked glycan.

Fucosylation of complex N-glycoside-linked sugar chains bound to the Fc region (or domain) of the SEA-CD40 antibody backbone is reduced. As used herein, a "complex N-glycoside-linked sugar chain" is typically bound to asparagine 297 (according to the EU index as set forth in Kabat, "Sequences of Immunological Interest, 5$^{th}$ Ed., Pub. No. 91-3242, U.S. Dept. Health & Human Services, NIH, Bethesda, Md., 1991). As used herein, the complex N-glycoside-linked sugar chain has a biantennary composite sugar chain, mainly having the following structure:

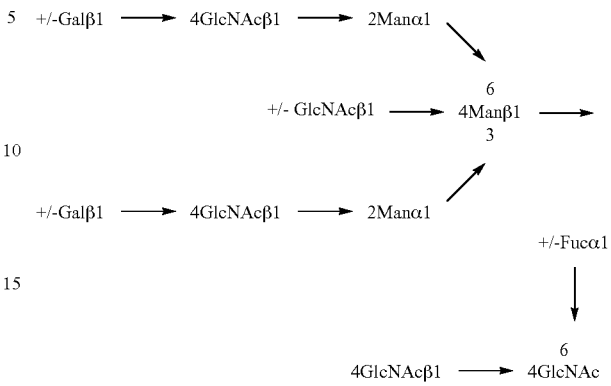

where ± indicates the sugar molecule can be present or absent, and the numbers indicate the position of linkages between the sugar molecules. In the above structure, the sugar chain terminal which binds to asparagine is called a reducing terminal (at right), and the opposite side is called a non-reducing terminal. Fucose is usually bound to N-acetylglucosamine ("GlcNAc") of the reducing terminal, typically by an α1,6 bond (the 6-position of GlcNAc is linked to the 1-position of fucose). "Gal" refers to galactose, and "Man" refers to mannose.

A "complex N-glycoside-linked sugar chain" includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of a high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s) of the SEA-CD40 molecule. For example, in various embodiments, less than about 60%, less than about 50%, less than about 40%, less than about 30%, less than about 20%, less than about 15%, less than about 10%, less than about 5%, or less than about 3% of the antibody has core fucosylation by fucose. In some embodiments, about 2% of the antibody has core fucosylation by fucose.

In certain embodiments, only a minor amount of a fucose analog (or a metabolite or product of the fucose analog) is incorporated into the complex N-glycoside-linked sugar chain(s). For example, in various embodiments, less than about 40%, less than about 30%, less than about 20%, less than about 15%, less than about 10%, less than about 5%, or less than about 3% of the SEA-CD40 antibody has core fucosylation by a fucose analog or a metabolite or product of the fucose analog. In some embodiments, about 2% of the SEA-CD40 antibody has core fucosylation by a fucose analog or a metabolite or product of the fucose analog.

Methods of making non-fucosylated antibodies by incubating antibody-producing cells with a fucose analogue are described, e.g., in WO/2009/135181. Briefly, cells that have been engineered to express the humanized S2C6 antibody are incubated in the presence of a fucose analogue or an intracellular metabolite or product of the fucose analog. As used herein, an intracellular metabolite can be, for example, a GDP-modified analog or a fully or partially de-esterified analog. A product can be, for example, a fully or partially de-esterified analog. In some embodiments, a fucose analogue can inhibit an enzyme(s) in the fucose salvage pathway. For example, a fucose analog (or an intracellular metabolite or product of the fucose analog) can inhibit the activity of fucokinase, or GDP-fucose-pyrophosphorylase. In some embodiments, a fucose analog (or an intracellular metabolite or product of the fucose analog) inhibits fucosyltransferase (preferably a 1,6-fucosyltransferase, e.g., the FUT8 protein). In some embodiments, a fucose analog (or an intracellular metabolite or product of the fucose analog) can inhibit the activity of an enzyme in the de novo synthetic pathway for fucose. For example, a fucose analog (or an intracellular metabolite or product of the fucose analog) can inhibit the activity of GDP-mannose 4,6-dehydratase or/or GDP-fucose synthetase. In some embodiments, the fucose analog (or an intracellular metabolite or product of the fucose analog) can inhibit a fucose transporter (e.g., GDP-fucose transporter).

In one embodiment, the fucose analogue is 2-flurofucose. Methods of using fucose analogues in growth medium and other fucose analogues are disclosed, e.g., in WO/2009/135181, which is herein incorporated by reference.

Other methods for engineering cell lines to reduce core fucosylation included gene knock-outs, gene knock-ins and RNA interference (RNAi). In gene knock-outs, the gene encoding FUT8 (alpha 1,6-fucosyltransferase enzyme) is inactivated. FUT8 catalyzes the transfer of a fucosyl residue from GDP-fucose to position 6 of Asn-linked (N-linked) GlcNac of an N-glycan. FUT8 is reported to be the only enzyme responsible for adding fucose to the N-linked biantennary carbohydrate at Asn297. Gene knock-ins add genes encoding enzymes such as GNTIII or a golgi alpha mannosidase II. An increase in the levels of such enzymes in cells diverts monoclonal antibodies from the fucosylation pathway (leading to decreased core fucosylation), and having increased amount of bisecting N-acetylglucosamines. RNAi typically also targets FUT8 gene expression, leading to decreased mRNA transcript levels or knocking out gene expression entirely. Any of these methods can be used to generate a cell line that would be able to produce a non-fucosylated antibody, e.g., an SEA-CD40 antibody.

Those of skill will recognize that many methods are available to determine the amount of fucosylation on an antibody. Methods include, e.g., LC-MS via PLRP-S chromatography and electrospray ionization quadrupole TOF MS.

The non-fucosylated antibody, SEA-CD40, when administered to a patient induces activation of monocyte maturation into macrophages and induce production of cytokines, including, e.g., interferon-γ (IFN-γ) and chemokine that elicit robust T-cell response to immune system challenges. Unlike fully agonistic antibodies, such as antibody 24.4.1., SEA-CD40 does not induce production of immune-dampening cytokines, such as interleukin-10 (IL-10). IL-10, in turn, induces activity of T-regulatory cells, which dampen the immune response. Thus, SEA-CD40 is useful for induction of a robust T-cell mediated immune response without promoting activity of T-regulatory cells.

Dosage and Administration of SEA-CD40

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically-compatible buffers to reduce discomfort at the site of injection. The solution can contain formulatory agents such as suspending, stabilizing and/or dispersing agents. Alternatively antibodies can be in lyophilized form for constitution with a suitable vehicle, e.g., sterile pyrogen-free water, before use.

SEA-CD40 is administered intravenously. In other embodiments, SEA-CD40 is administered subcutaneously. In a further embodiment, SEA-CD40 is administered subcutaneously at the site of a tumor.

The non-fucosylated SEA-CD40 antibody has surprisingly enhanced immune activation activity as compared to its parent antibody, dacetuzumab. Thus, SEA-CD40 can be administered to patients at lower doses and on different schedules as compared to dacetuzumab.

As an example, SEA-CD40 can be adminstered to patients at levels between 0.1-2000 μg/kg (μg antibody per kilogram patient body weight). Other possible dosage ranges are 10-1000 μg/kg, 50-800 μg/kg, 75-600 μg/kg, 100-500 μg/kg. Other possible dosage ranges are the following: 100-300 μg/kg, 300-500 μg/kg, 500-700 μg/kg, 700-900 μg/kg, and 900-1100 μg/kg. Still more dose ranges are the following: 100-150 μg/kg, 150-200 μg/kg, 200-250 μg/kg, 250-300 μg/kg, 300-350 μg/kg, 350-400 μg/kg, 400-450 μg/kg, 450-500 μg/kg, 500-550 μg/kg, 550-600 μg/kg, 600-650 μg/kg, 650-700 μg/kg, 700-750 μg/kg, 750-800 μg/kg, 800-850 μg/kg, 850-900 μg/kg, 900-950 μg/kg, 950-1000 μg/kg, 1000-1050 μg/kg, and 1050-1100 μg/kg. Other possible dosage ranges are 0.3-200 μg/kg, 0.6-150 μg/kg, 1.0-100 μg/kg, 2-50 μg/kg, 5-25 μg/kg, 7.5-15 μg/kg, and 8-12 μg/kg.

In other embodiments, SEA-CD40 is administered to patients at 0.6 μg/kg, 1.0 μg/kg, 2.5 μg/kg, 5.0 μg/kg, 7.5 μg/kg, 10 μg/kg, 30 μg/kg, 50 μg/kg, 75 μg/kg, 100 μg/kg, or 200 μg/kg. In a preferred embodiment, SEA-CD40 is administered to patients at 10 μg/kg.

In further embodiments, SEA-CD40 is administered to patients at about 60 μg/kg, about 100 μg/kg, about 150 μg/kg, about 200 μg/kg, about 250 μg/kg, about 300 μg/kg, about 350 μg/kg, about 400 μg/kg, about 450 μg/kg, about 500 μg/kg, about 550 μg/kg, about 600 μg/kg, about 650 μg/kg, about 700 μg/kg, about 750 μg/kg, about 800 μg/kg, about 850 μg/kg, about 900 μg/kg, about 950 μg/kg, about 1000-1050 μg/kg, about 1050 μg/kg, and 1110 μg/kg.

In some embodiments, SEA-CD40 is administered in a manner to reduce the likelihood of immune exhaustion. For example, SEA-CD40 can be administered at three week intervals, six week intervals, eight week intervals, ten week intervals, twelve week intervals, or 14 week intervals. Intervals can also be on a monthly schedule, e.g., one month intervals, two month intervals, or three month intervals.

Because SEA-CD40 activates the immune system to respond against tumor-related antigens, its use is not limited to cancers that express CD40. Thus SEA-CD40 can be used to treat both CD40 positive and CD40 negative cancers.

SEA-CD40 is preferably used to treat tumors that are known to be immune responsive, particularly if the cancer expresses low levels of CD40 or does not detectably express CD40. Immune responsive cancers include, e.g., melanoma; bladder cancer; lung cancer, e.g., small cell lung cancer and non-small cell lung cancer; ovarian cancer; kidney cancer; pancreatic cancer; breast cancer; cervical cancer; head and neck cancer, prostate cancer; glioblastoma; non-hodgkin lymphoma; chronic lymphocytic leukemia; hepatocellular carcinoma; or multiple myeloma.

In another embodiment, SEA-CD40 is used to treat solid tumors. In a further embodiment, SEA-CD40 is used to treat blood cancers, e.g., lymphoma, including non-Hodgkin lymphoma and Hodgkin lymphoma; chronic lymphocytic leukemia; or multiple myeloma.

In one embodiment, SEA-CD40 is administered to cancer patients with CD40-negative cancer at 30 µg/kg. A preferred dosing schedule is intravenous administration of 30 µg/kg of SEA-CD40 on days one and eight of a three week cycle. The total number of cycles is determined by a physician. Another preferred dosing cycle is intravenous administration of 30 µg/kg of SEA-CD40 on day one of a three week cycle. The total number of cycles is determined by a physician. In another embodiment, intravenous administration of 30 µg/kg of SEA-CD40 is performed on days one and eight of a three week cycle for two cycles. For subsequent cycles, SEA-CD40 is adminstered at 30 µg/kg on day one of the three week cycle, with the total number of cycles determined by a physician. CD40-negative cancers can be, e.g., a melanoma, a breast cancer, including metastatic breast cancer, a lung cancer, including a non-small cell lung cancer, or pancreatic cancer. CD40-negative cancers can also be blood or hematologic cancers, such as lymphomas, e.g., T-cell lymphomas. Other blood or hematologic cancers include, e.g., chronic lymphocytic leukemia; or multiple myeloma.

In one embodiment, SEA-CD40 is administered to cancer patients with CD40-positive cancer at 30 µg/kg. A preferred dosing schedule is intravenous administration of 30 µg/kg of SEA-CD40 on days one and eight of a three week cycle. The total number of cycles is determined by a physician. Another preferred dosing cycle is intravenous administration of 30 µg/kg of SEA-CD40 on day one of a three week cycle. The total number of cycles is determined by a physician. In another embodiment, intravenous administration of 30 µg/kg of SEA-CD40 is performed on days one and eight of a three week cycle for two cycles. For subsequent cycles, SEA-CD40 is adminstered at 30 µg/kg on day one of the three week cycle, with the total number of cycles determined by a physician. CD40-positive cancers can be, e.g., a melanoma, a breast cancer, including metastatic breast cancer, a lung cancer, including a non-small cell lung cancer, bladder cancer, or pancreatic cancer. CD40-positive cancers can also be blood or hematologic cancers, e.g., B-cell lymphomas, such as Hodgkin lymphoma, diffuse large B-cell lymphoma, or indolent lymphoma, including follicular lymphoma. Other blood or hematologic cancers include, e.g., chronic lymphocytic leukemia; or multiple myeloma.

SEA-CD40 Combination Therapy

Because of its immune stimulatory function, SEA-CD40 can be used in combination with other therapeutic agents that activate the immune system. Drugs with immune stimulatory function include, e.g., T-cell modulators, including immune checkpoint inhibitors; immune activators; and chemotherapeutic agents that induce immunogenic cell death. As an example, certain antibodies function by blocking activity of molecules that serve as immune checkpoints on T cells. SEA-CD40 can, therefore be used in combination with antibodies that target immune checkpoint proteins.

T-Cell Modulators

T-cells play a role in the ability of the immune system to recognize and eliminate cancers from the body. T-cell modulators include antibodies that block the function of immune checkpoints. See, e.g., Pardo11, *Nature Rev. Cancer,* 12:252-264 (2012). Antibodies that block immune checkpoints include, e.g., anti-PD-1 antibodies, anti-PD-L1 antibodies, and anti-CTLA4 antibodies. Other checkpoint inhibitors/activators include LAG3 and TIM3. Antibodies against some proteins can be used to modulate T-cell activity or preferably activate T-cell activity, e.g., antibodies against 41BB, CD27, ICOS, and OX40. Other T-cell modulators include inhibitors of the enzyme indolamine 2,3-dioxygenase (IDO).

Anti-CTLA4 antibodies recognize the protein cytotoxic lymphocyte 4 (CTLA-4), also known as cluster of differentiation 152 or CD152. The CTLA-4 protein is expressed on T cells, which recognize antigens that are suitable for attack by the immune system. Activation of CTLA-4 dampens the immune response. See e.g., Nirschi and Drake, *Clin. Cancer Res.,* 19:4917-4924 (2013). Antibodies specific for CTLA-4 and that block its activity have been used to treat cancer by upregulating the immune response to cancers. Examples of CTLA-4 antibodies include ipilimumab or tremelimumab. SEA-CD40 can be administered in combination with ipilimumab or tremelimumab to treat cancer.

Anti-PD1 antibodies recognize the protein programmed death-1 (PD-1). Like CTLA-4, PD-1 is expressed on T cells, and dampens the immune response. See e.g., Nirschi and Drake, *Clin. Cancer Res.,* 19:4917-4924 (2013). Antibodies specific for PD-1 and that block its activity have been used to treat cancer by upregulating the immune response to cancers. Examples of PD-1 antibodies include MEDI0680, AMP-224, nivolumab, pembrolizumab, and pidilizumab. Other PD-1 binding proteins that act as checkpoint inhibitors and can be used in combination with SEA-CD40 include, e.g., B7-DC-Fc. SEA-CD40 can be administered in combination with MEDI0680, AMP-224, nivolumab, pembrolizumab, or pidilizumab to treat cancer.

PD-L1 is a ligand of the PD-1 protein. PD-L1 is expressed on cancer cells and its interaction with PD-1 allows PD-L1-expressing cancer cells to evade the immune system. Anti-PD-L1 antibodies have been generated and used to treat cancer. Examples of PD-L1 antibodies include, e.g., MEDI4736, BMS-936559/MDX-1105, MSB0010718C and MPDL3280A. SEA-CD40 can be administered in combination with MEDI4736, BMS-936559/MDX-1105, MSB0010718C or MPDL3280A to treat cancer.

Other antibodies that block the function of immune checkpoint proteins include antibodies directed against e.g., LAG3 and TIM3, and can be used in combination with SEA-CD40.

Antibodies against 41BB, CD27, ICOS, and OX40 are used to activate T-cell activity and can be used in combination with SEA-CD40. OX40 antibodies include, e.g., MEDI6469 and MEDI6383. An example of an agonistic anti-CD27 antibody is CDX-1127, which can be used in combination with SEA-CD40.

The enzyme indolamine 2,3-dioxygenase (IDO) catalyzes the degradation of the amino acid tryptophan. Inhibitors of IDO can be small molecules, such as rosmarinic acid, COX-2 inhibitors, and alpha-methyl-tryptophan.

Chemotherapeutic Agents that Induce Immunogenic Cell Death

In most humans, millions of cells die via apoptosis and are removed without generating an immune response. However, after treatment with some chemotherapeutic agents, immune cells have been observed to infiltrate tumors. Thus, some tumor cells killed by chemotherapeutic agents act as vaccines and raise a tumor-specific immune response. This phenomenon is referred to as immunogenic cell death (ICD). See, e.g., Kroemer et al., *Annu. Rev. Immunol.*, 31:51-72 (2013). The ability of a chemotherapeutic agent to induce ICD can be determined experimentally. Two criteria must be met. First, injection of an immunocompetent mouse with cancer cells that have been treated in vitro with a chemotherapeutic agent must elicit a protective immune response that is specific for tumor antigens, in the absence of adjuvant. Second, ICD occurring in vivo, e.g., a mouse syngeneic model with treatment using a potential ICD-inducing chemotherapeutic agent, must drive an immune response in the tumor that is dependent on the immune system.

Chemotherapeutic agents that induce ICD include, e.g., anthracyclines, anti-EGFR antibodies, bortezomib, cyclophosphamide, gemcitabine, irradiation of the tumor, and oxaliplatin. SEA-CD40 can be used in combination with any of these agents to generate an enhanced immune response and treat cancer in a patient.

Immune Activation

Cancer can is also treated by administering agents that directly stimulate the immune system. Such agents include, e.g., GM-CSF, IFN-gamma, interleukin-2, GVAX, and TLR9 agonists. Other immune activators include, e.g., cancer vaccines, Bacillus Calmette-Guérin (BCG), nonspecific immunostimulants (e.g. imiquimod) and cellular therapies like CAR-T cells. SEA-CD40 can be used in combination with any of these agents to generate an enhanced immune response and treat cancer in a patient.

Other Combinations

Other combinations with SEA-CD40 can be used to treat cancer. Examples include, e.g., SEA-CD40 in combination with an anti-PD1 antibody, e.g., nivolumab, pembrolizumab, and pidilizumab, MEDI0680, or AMP-224; SEA-CD40 in combination with Gemcitabine, with or without paclitaxel or cisplatin or oxaliplatin; SEA-CD-40 in combination with a BRAF inhibitor, e.g., vemurafenib or dabrafenib; or SEA-CD40 in combination with cyclophosphamide, ADRIAMYCIN™, vincristine, and prednisone (CHOP) or rituximab, ifosfamide, carboplatin, and etopiside (RICE) or rituximab, gemcitabine, dexamethasone and cisplatin (RGDP).

EXAMPLES

The following examples are offered to illustrate, but not to limit the claimed invention.

Example 1: Synthesis of Non-Fucosylated hS2C6 Antibody

The humanized anti-CD40 antibody, S2C6 with heavy and light chains of SEQ ID NOs: 1 and 2 was expressed in CHO cells. A fucosylation inhibitor, 2-fluorofucose, was included in the cell culture media during the production of antibodies resulted in non-fucosylated antibody, SEA-CD40. See, e.g., Okeley et al., *Proc. Nat'l Acad. Sci.* 110:5404-55409 (2013). The base media for cell growth was fucose free and 2-flurofucose was added to the media to inhibit protein fucosylation. Ibid. Incorporation of fucose into antibodies was measured by LC-MS via PLRP-S chromatography and electrospray ionization quadrople TOF MS. Ibid. Data not shown.

Example 2: Characterization of Non-Fucosylated hS2C6 Antibody

CD40 Binding Affinity Determination of SEA-CD40:

For isolation of peripheral blood mononuclear cells (PBMCs), human whole blood was supplied by ASTARTE BIOLOGICS™. Briefly, blood was collected into heparin tubes and delivered to SEATTLE GENETICS™ within four hours of being drawn. Upon arrival blood was aliquoted into 50 ml conical tubes (falcon) and spun at 200 g in an EPPENDORF™ 5810R (A-4-62 rotor) for 20 minutes at 25° C., without break to separate the platelet rich fraction. Following centrifugation, three distinct layers were formed: bottom layer, red blood cells (accounting for 50-80% of the total volume); middle layer, very thin band of white blood cells; top layer, straw-colored platelet rich plasma (PRP).

The upper straw colored layer with which is enriched in platelets was removed with a one ml pipette. Once the platelet rich plasma was removed blood was diluted with equal volumes of sterile PBS (GIBCO™, lot 1618435, ept 2016-07). 15 mls of HISTOPAQUE™-1077 (SIGMA™, lot number RNBD2965, Expt. 5/2017) warmed to room temperature was underlayered below the blood. HISTOPAQUE™ samples were spun at 1500 rpm for 25 minutes at 25° C. with outbreak. Following centrifugation three layers are formed again: bottom layer, red blood cells (accounting for 50-80% of the total volume); middle layer, thick band of white blood cells (also called "buffy coat"); top layer, PBS and remaining platelets.

The upper PBS/Platelet layer was removed with a 1 ml pipet and discarded. The thick band of white blood cells was gently removed and placed into a clean 50 ml sterile conical tube. Tubes were filled to 50 mls and cells are spun at 800 g for 10 minutes. Wash solution was removed and pellets were resuspended in 10 mls of ACK red blood lysis buffer (GIBCO™, lot 1618488) for ten minutes. Fifty milliliter conical tubes were then topped off with 35 ml sterile PBS and cells were spun at 800 g for ten minutes. The wash solution was removed and pellet was resuspended in 50 mls of PBS. Five hundred µl of sample was removed and PBMC were counted with a Vi-cell-XR (BECKMAN COULTER™). Cells were spun again at 800 g for ten minutes. The wash solution was removed and pellet re-suspended at 1×106/ml in FACs staining solution (BD™). One hundred µl of resuspended PBMC's were plated into a 96 well U-bottom plate (CORNING™) and placed on ice. To block non-specific FcγRIIIa binding, PBMC's were pre-treated 100 µg/ml of human Fc-fragments (CALBIOCHEM™) for thirty minutes. Ten-fold serial dilutions of biotinylated SEA-h00 (non-fucosylated control antibody), SEA-CD40, or SGN-40 were prepared to create a dilution series of (100, 10, 1, 0.1, 0.01, 0.001, 0.0001 µg/ml).

Samples were washed twice in ice cold FACs buffer and incubated with saturating concentrations of PE-Streptavidin (BD™) on ice for thirty minutes. Samples were washed twice in ice cold FACs buffer and re-suspended in 200 µl of FAC's buffer. Binding was assessed using a BD LSRII and DIVA software. FCS were analyzed in FLOWJO™ and GeoMean fluorescence of positively stained cells was determined and plotted in Prism Graph Pad. Data was fit to non-linear regression assuming one binding site in Prism and binding KD values calculated by dividing µg/ml calculation by molecular weight of SEA-CD40.

Results:

The binding affinity of SEA-CD40, and the parental antibody dacetuzumab, to CD40 on human peripheral blood mononuclear cells (PBMC) was determined by flow cytometry. Background binding of an appropriate isotype control was subtracted and mean fluorescence intensity (MFI) was plotted against antibody concentration. Results are shown in FIG. 1. SEA-CD40 and the parental antibody dacetuzumab gave virtually overlapping binding curves and both saturated PBMC's at concentrations of approximately 1.17 nM. These data suggest that changes in fucosylation do not affect SEA CD40 affinity for CD40.

FcγRIIIa Binding Affinity Determination of SEA-CD40:

CHO cells that express the high (158V) or low (158F) version of human FcγRIIIa were generated. 20×106 cells were centrifuged, washed once in 20 ml 1+ PBS, and resuspended in 8 ml BD™ stain buffer. Cells were aliquoted in the following density: 2.0×106 cells/ml in 100 ul volume. 0.20×106 cells were aliquoted to each well. Cells were centrifuged at 1250 rpm, for five minutes at room temperature.

Antibodies were diluted to either 0.14 ug/ml (SGN) or 0.04 ug/ml (SEA). Dilutions are provided in Table 1.

TABLE 1

| Biotinylated abs dilutions | Conc. Mg/ml | Vol (ul) antibody | Vol. stain buffer | Highest stain conc ug/ml |
|---|---|---|---|---|
| SGN-40-Biotin | 3.29 | 18.23 | 581.7 | 100 |
| SEA40-Biotin | 3.27 | 15.11 | 584.7 | 100 |
| h00-SGN-Biotin | 1.55 | 38.7 | 561.0 | 100 |
| h00-SEA biotin | 3.61 | 16.6 | 583 | 100 |

Supernatants were aspirated from the spun cells and 60 ul of corresponding antibody dilutions were added with a multichannel pipet. Corresponding concentrations were 100, 33.3, 11.1, 3.7, 1.23, 0.41, 0.14 mcg/ml. Samples were incubated at 4° C. for 1 hour. Samples were centrifuged, and washed twice with 200 μl BD™ stain buffer per well. One milliliter of Streptavidin-PE was added to 20 ml BD stain buffer (excess 2°) to make streptavidin buffer. 100 μl of streptavidin buffer was added to each sample and they were incubated for 30 min in the dark at 4° C. Samples were then centrifuged and washed twice with 200 ul BD™ Stain buffer per well. Samples were analyzed by Flow cytometry in HTS mode on the LSRII and graph MFI to calculate Kd's in PRIZM.

Figures 2A, 2B:
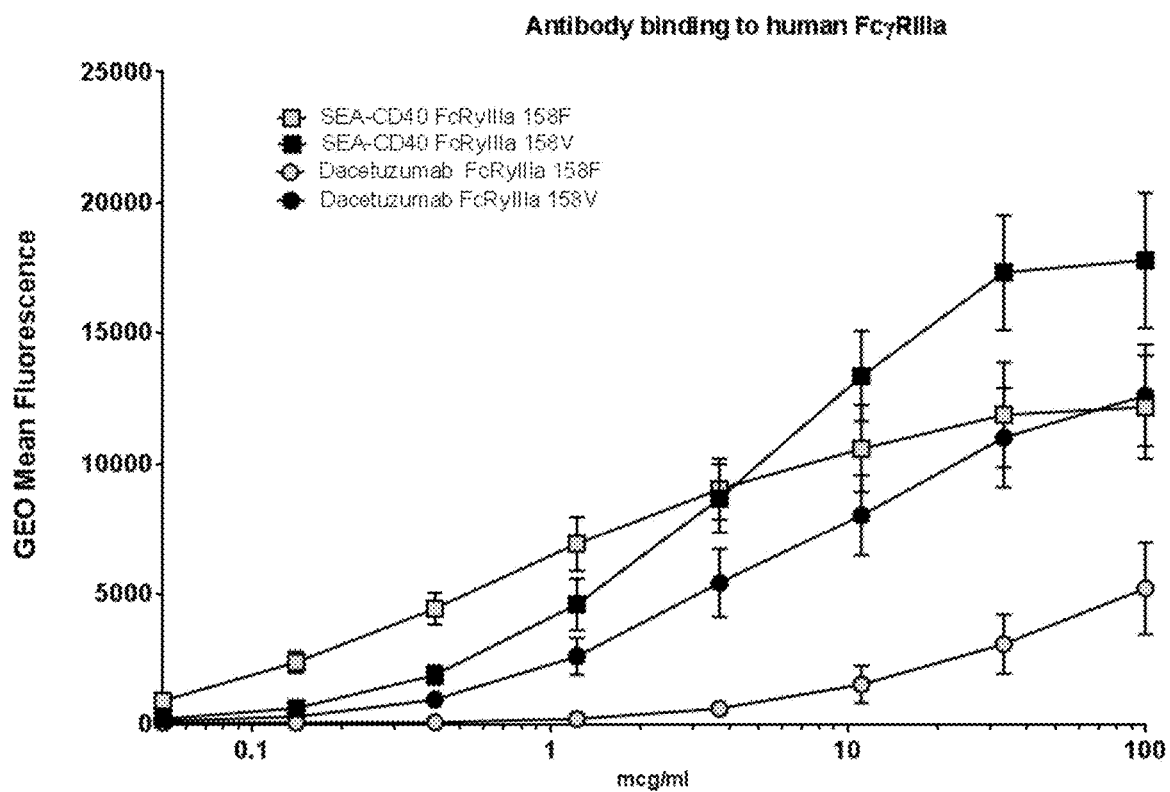
FIGS. 2A and 2B provides the binding affinities of SEA-CD40 (open and closed squares) and dacetuzumab (open and closed circles) for the human FcγIIIa receptor variants.
Figure 3:
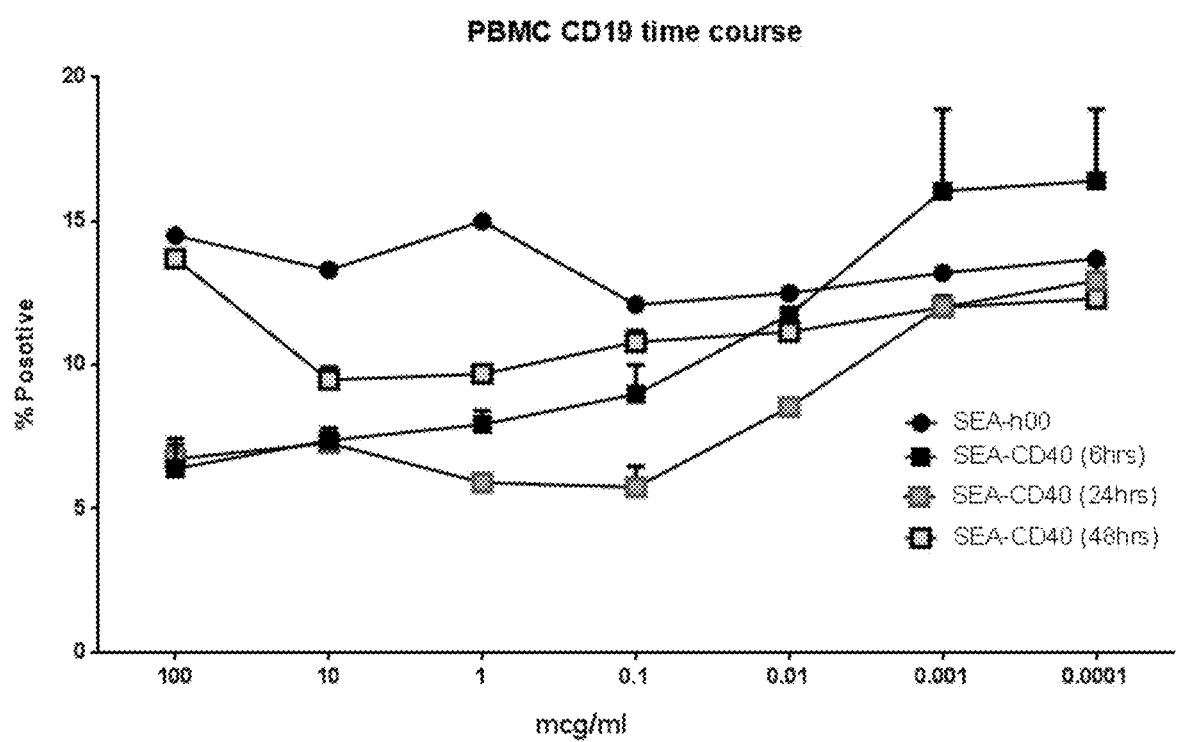
FIG. 3 provides a dose relationship and time course of B-cell depletion from human peripheral blood mononuclear cells (PBMCs) as a result of treatment with SEA-CD40.

Results:

Binding of SEA-CD40 and the parent antibody dacetuzumab to Chinese hamster ovary (CHO) cells expressing the low (158F) or high (158V) affinity form of FcγRIIIa was assessed. Results are shown in FIGS. 2A and 2B. SEA-CD40 bound to both the low (158F) and high (158V) form of FcγRIIIa with similar affinity ($K_D$ 27.5 nM and 5.2 nM, respectively). SEA-CD40 binding to the low affinity (158F) form was significantly better than the fucosylated parental antibody dacetuzumab ($K_D$ 302.7 nM), and SEA-CD40 even bound the high affinity 158V form better than the fucosylated dacetuzumab parent (5.2 nM vs. 37.9 nM respectively).

SEA-CD40 Mediated ADCC Activity:

Human PBMC's were isolated as above and were treated with various concentrations of SEA-CD40 or an SEA-isotype control (SEA-h00) for 6, 24, or 48 hours. Cultures were stained for CD19+ B cells and cell numbers were quantified by flow cytometry.

Results:

Human PBMC cultures, were treated with 100, 10, 1, 0.1, 0.01, 0.001, or 0.0001 μg/mL of SEA CD40 or a non-binding SEA-isotype control (SEA-h00) for 6, 24, and 48 hours and the number of CD40 positive cells were then assessed. Results are shown in FIG. 4. SEA-CD40 treatment resulted in a significant decrease in CD40+ CD19+ B cells in a dose- and time-dependent manner, even down to low sub μg/mL concentrations. There was no significant effect of SEA-CD40 on monocyte/DC numbers (monocyte/DC data not shown).

Assessment of Cytokine Production in Human Whole Blood or PBMCs:

Human whole blood was supplied by ASTARTE BIOLOGICS™. Briefly, 100 mls of blood was collected into heparin tubes and delivered to SEATTLE GENETICS™ within 4 hours of the draw. Half of the blood was set aside for whole blood cultures while the other half was used to isolate PBMCs as described above. One hundred μl of whole blood was aliquoted into 3-96 flat bottom tissue culture plates (COSTAR™). Isolated PBMCs were counted in a VIACELL™ and resuspended at 1×10$^6$ cells/ml in DMEM containing 10% FBS (Atlanta Biologics), 1× penicillin/strepA, and X glutamine (PBMC media). For PBMCs, one hundred μl of resuspended, purified PBMCs were aliquoted into 3-96 flat bottom tissue culture plates. 10× serial dilutions of SEA-h00 and SEA-CD40 were made in PBMC media and whole blood and isolated PBMC cultures were treated with descending concentrations of either SEA-h00 or SEA-CD40 (100, 10, 1.0, 0.1, 0.01, 0.001, 0.0001 or 0 μg/ml). SEA-CD40 treatment was performed in duplicate for both whole blood and PBMC cultures at each time point. At each of the pre-determined times points (6, 24, and 48 hours) a 96 well plate containing whole blood or purified PBMCs was spun with a plate adapter in an Eppendorf 5810R at 800 rpm for 5 minutes. Serum or tissue culture supernatants were removed and transferred to a 96 strip tube rack and samples were frozen at −80° C. until processing.

Frozen tissue culture supernatants and serum were thawed overnight at 4° C. and processed for cytokine production using a LUMINEX™ multiplex Kit from MILLIPORE™. Custom kits were designed to analyze IFNγ, IL-12p40, IL-6, IL-8, MCP-1, MIP-1α, IL-1β, MIP-1β, TNF-α, sCD40L. Analytes were picked based on cytokines observed with dacetuzemab in previous studies. Tissue culture supernatants and serum samples were processed as per the manufactures instructions. Briefly, assay plates were washed with 200 μL of wash buffer per well, followed by addition of 25 μL standard or buffer, 25 μL matrix or sample, and 25 μL of multiplexed analyte beads to each well. Samples were incubated overnight with vigorous shaking at 4° C. Plates are washed the assay plates twice with wash buffer. Twenty-five μL of detection antibodies were added to each well and incubated at room temperature for one hour. Twenty-five μL of streptavidin-phycoerythrin (SA-PE) were added and samples incubated at room temperature for thirty minutes. The plate was washed twice with wash buffer and beads were resuspended with 150 μL of sheath fluid. The samples were analyzed using LUMINEX™ MAGPIX™ systems in combination with the XPONENT™ software system. Cytokine levels were calculated from the standard curve.

Figure 4A:
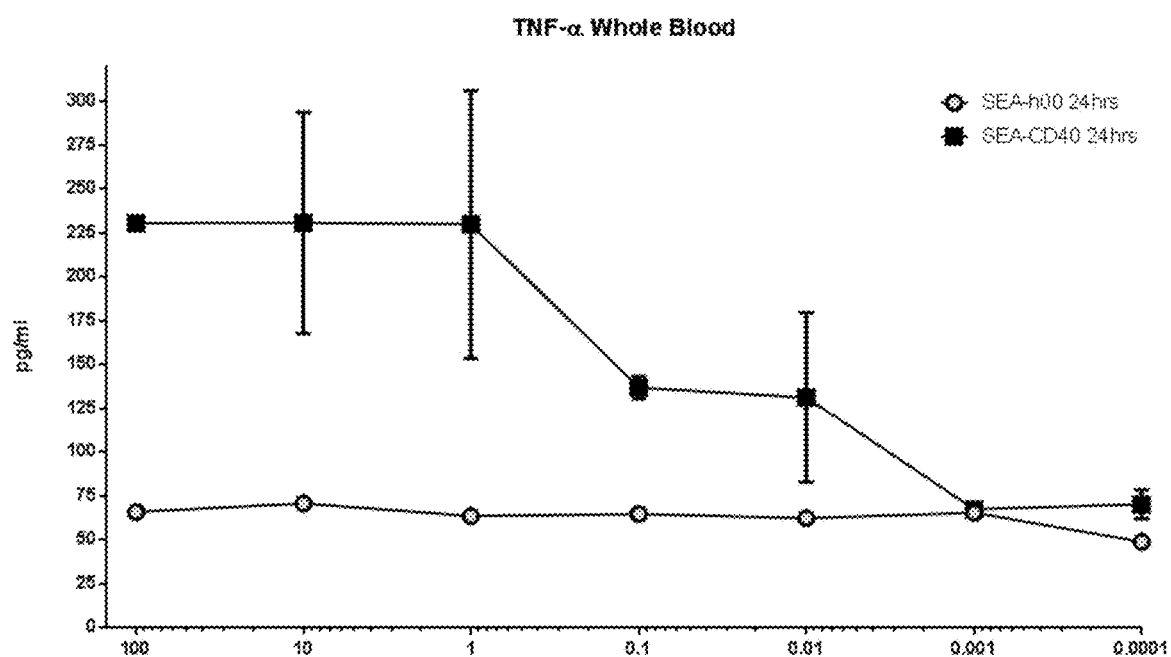
FIGS. 4A and 4B demonstrate representative cytokine production by human whole blood after twenty-four hours of treatment with SEA-CD40 or an isotype control (SEA-h00). Antibodies were adminstered in units of µg/ml.
Figure 4B:
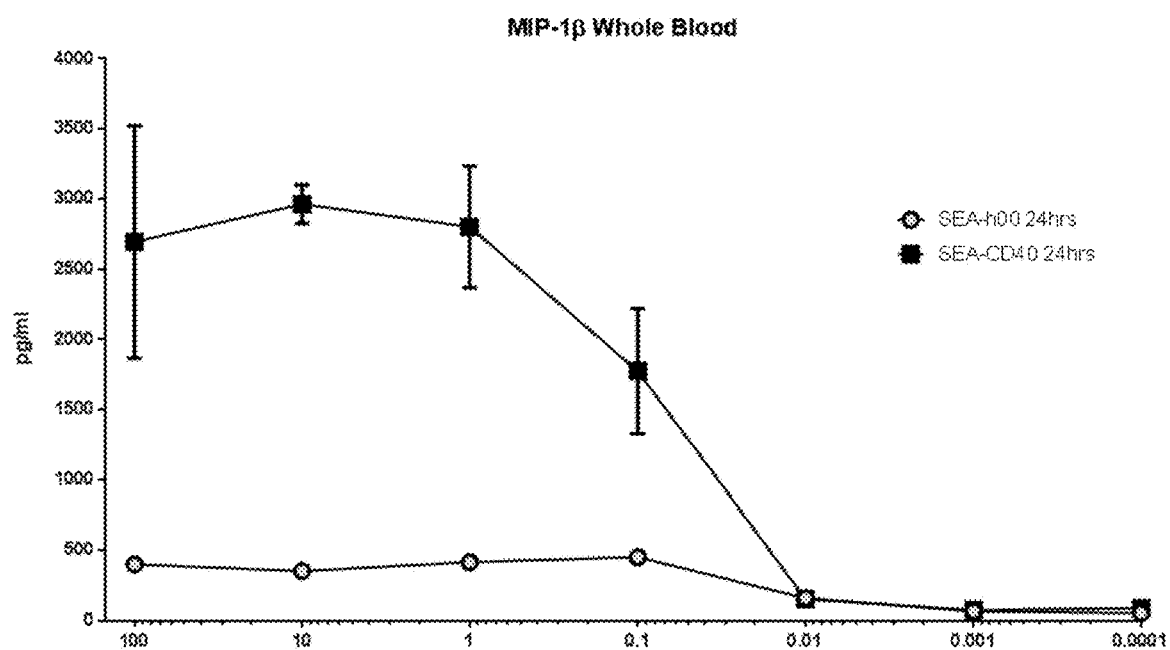

Results:

Human whole blood cultures were treated with a SEA-isotype control or SEA-CD40 (100, 10, 1, 0.1, 0.01, 0.001, or 0.0001 μg/mL) for 6, 24, or 48 hours. Serum or tissue culture supernatants were collected and inflammatory cytokines assessed by multiplexed LUMINEX™ analysis. The data are plotted as a fold increase in cytokine production compared to a SEA-isotype control. SEA-CD40 stimulated robust production of IFNγ, MIP1β, and TNFα at 6, 24, and 48 hours in whole blood, as shown in Table 2, below. SEA-CD40 levels are provided in the leftmost columns. Activity was observed at levels as low as 0.010 µg/mL SEA-CD40. Stimulation of MIP1β, and TNFα at twenty-four hours are shown in FIGS. 4A and 4B.

TABLE 2

| Whole Blood | | | | | | |
|---|---|---|---|---|---|---|
| | IFNγ | IL-8 | MCP-1 | MIP1α | MIP1β | TNFα |
| 6 hrs | | | | | | |
| 100.00 | 4.52 | 2.01 | 2.75 | 1.30 | 30.86 | 3.22 |
| 10.00 | 10.81 | 1.05 | 2.33 | 1.04 | 26.69 | 1.90 |
| 1.00 | 4.99 | 1.13 | 1.62 | 0.93 | 4.59 | 2.20 |
| 0.10 | 3.42 | 0.84 | 0.96 | 1.02 | 0.88 | 1.65 |
| 0.01 | 1.83 | 1.00 | 1.29 | 1.26 | 0.96 | 0.98 |
| 0.00 | 1.20 | 0.94 | 1.25 | 1.24 | 0.93 | 1.04 |
| 0.00 | 1.16 | 1.05 | 1.29 | 1.15 | 0.98 | 1.02 |
| 24 hr | | | | | | |
| 100.00 | 3.01 | 1.95 | 2.19 | 2.28 | 6.77 | 3.51 |
| 10.00 | 3.23 | 1.52 | 2.84 | 2.34 | 8.42 | 3.26 |
| 1.00 | 2.31 | 1.70 | 2.36 | 1.75 | 6.77 | 3.62 |
| 0.10 | 1.32 | 1.36 | 1.19 | 0.89 | 3.95 | 2.12 |
| 0.01 | 0.95 | 1.10 | 1.01 | 0.74 | 0.96 | 2.11 |
| 0.00 | 0.55 | 0.92 | 1.04 | 0.95 | 1.15 | 1.03 |
| 0.00 | 0.40 | 0.82 | 0.79 | 1.01 | 1.66 | 1.44 |
| 48 hrs | | | | | | |
| 100.00 | 3.59 | 1.11 | 1.19 | 1.26 | 2.03 | 3.47 |
| 10.00 | 2.37 | 1.21 | 1.22 | 1.24 | 2.27 | 2.71 |
| 1.00 | 2.15 | 1.08 | 1.07 | 1.07 | 1.76 | 2.63 |
| 0.10 | 1.01 | 0.76 | 1.05 | 1.09 | 1.43 | 2.53 |
| 0.01 | 0.86 | 0.81 | 1.16 | 1.17 | 1.27 | 1.93 |
| 0.00 | 0.87 | 0.97 | 1.18 | 1.18 | 0.97 | 1.18 |
| 0.00 | 0.96 | 0.93 | 0.87 | 1.05 | 0.68 | 1.17 |

Figure 5A:
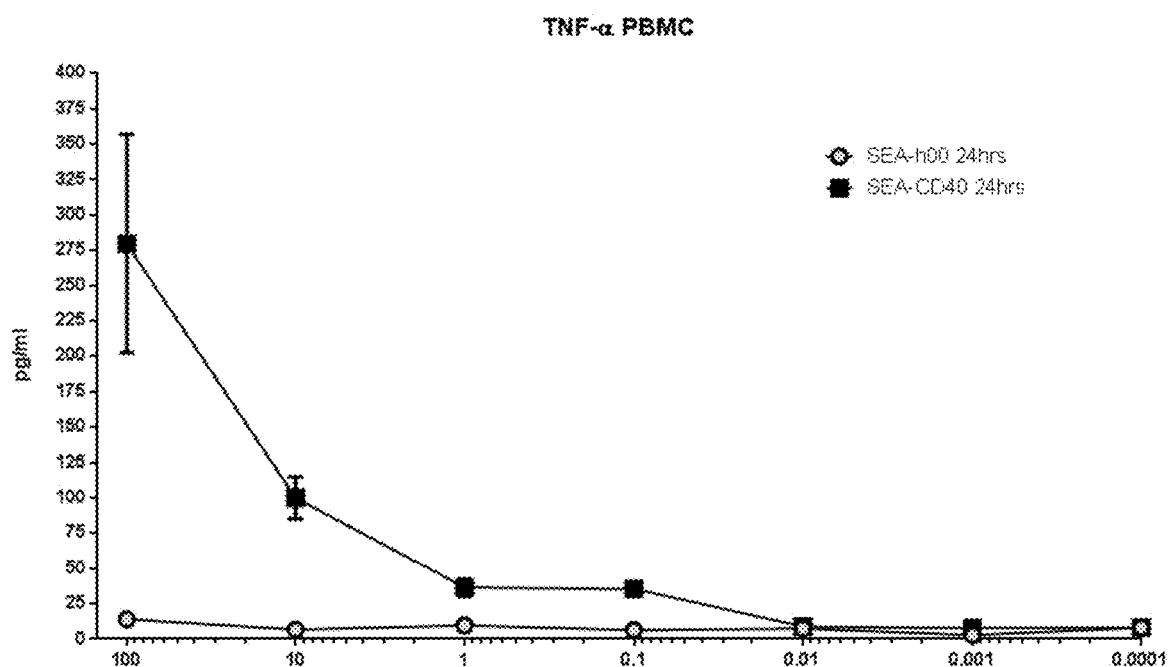
FIGS. 5A and 5B demonstrate representative cytokine production by human PBMCs after twenty-four hours of treatment with SEA-CD40 or an isotype control (SEA-h00). Antibodies were adminstered in units of µg/ml.
Figure 5B:
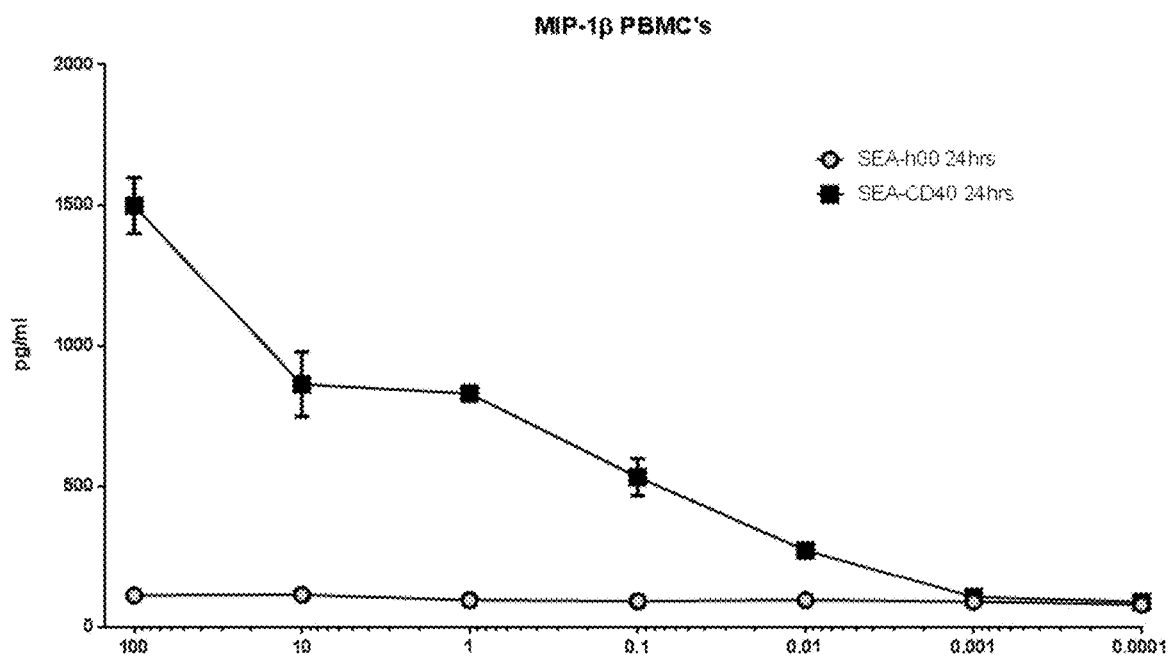

Human PBMC were treated with a SEA-isotype control or SEA-CD40 (100, 10, 1, 0.1, 0.01, 0.001, or 0.0001 µg/mL) for 6, 24, or 48 hours. Serum or tissue culture supernatants were collected and inflammatory cytokines assessed by multiplexed LUMINEX™ analysis. The data are plotted as a fold increase in cytokine production compared to a SEA-isotype control. SEA-CD40 stimulated robust production of IFNγ, MIP1β, and TNFα at 6, 24, and 48 hours PBMCs, as shown in Table 3, below. SEA-CD40 levels, in µg/mL, are provided in the leftmost columns. Activity was observed at levels as low as 0.010 µg/mL SEA-CD40. Stimulation of MIP1β, and TNFα at twenty-four hours are shown in FIGS. 5A and 5B.

TABLE 3

| PBMC | | | | | | |
|---|---|---|---|---|---|---|
| | IFNγ | IL-8 | MCP-1 | MIP1α | MIP1β | TNFα |
| 6 hr | | | | | | |
| 100 | 8.75 | 1.18 | 3.00 | 2.51 | 6.91 | 11.66 |
| 10 | 13.68 | 1.16 | 7.70 | 3.11 | 11.59 | 17.72 |
| 1 | 6.21 | 0.89 | 2.71 | 1.48 | 4.55 | 5.58 |
| 0.1 | 3.89 | 0.89 | 1.61 | 1.26 | 3.40 | 3.04 |
| 0.01 | 1.49 | 0.75 | 1.07 | 1.26 | 2.11 | 2.26 |
| 0.001 | 1.60 | 0.71 | 0.89 | 1.31 | 1.30 | 1.28 |
| 0.0001 | 1.58 | 0.71 | 0.77 | 0.83 | 1.33 | 1.10 |
| 24 hr | | | | | | |
| 100 | 8.51 | 4.79 | 5.69 | 2.84 | 13.43 | 19.91 |
| 10 | 8.98 | 3.96 | 7.87 | 1.91 | 7.58 | 14.97 |

TABLE 3-continued

| PBMC | | | | | | |
|---|---|---|---|---|---|---|
| | IFNγ | IL-8 | MCP-1 | MIP1α | MIP1β | TNFα |
| 1 | 3.32 | 1.35 | 3.10 | 1.28 | 8.73 | 3.79 |
| 0.1 | 1.80 | 1.04 | 1.38 | 1.03 | 5.85 | 5.58 |
| 0.01 | 1.66 | 0.85 | 1.28 | 1.08 | 2.87 | 1.22 |
| 0.001 | 1.12 | 0.71 | 0.90 | 0.96 | 1.18 | 2.75 |
| 0.0001 | 0.40 | 0.71 | 0.80 | 0.74 | 1.11 | 1.02 |
| 48 hrs | | | | | | |
| 100 | 17.92 | 2.58 | 11.47 | 1.51 | 2.81 | 14.02 |
| 10 | 8.81 | 3.61 | 3.39 | 1.46 | 2.33 | 5.58 |
| 1 | 4.09 | 2.07 | 2.36 | 1.32 | 1.91 | 6.47 |
| 0.1 | 1.82 | 1.19 | 0.84 | 0.96 | 1.00 | 2.30 |
| 0.01 | 1.03 | 1.02 | 1.41 | 0.95 | 1.13 | 2.09 |
| 0.001 | 0.83 | 0.86 | 1.13 | 0.93 | 0.96 | 1.93 |
| 0.0001 | 0.82 | 0.97 | 0.97 | 0.91 | 1.05 | 1.73 |

Assessment of Activation Markers on PBMCs:

Co-stimulatory molecule surface expression was assessed on the cell pellets remaining from the cytokine analysis described above. Cell pellets were resuspended in 50 ml of BD™ FACs buffer and transferred to and 96 well round bottomed microtiter plates Fc receptors were blocked with human 100 ug/ml Fc-fragments (MILLIPORE™) for 30 minutes on ice. A master mix composed of PE-CD86 (BD) and MHCII (Pan anti-DR,DP,DQ antibody BD) diluted at 1:100 was prepared in BD™ FACs buffer containing 100 mg/ml human Fc fragments. Five µl of the master mix was added to each well containing ninety µl and samples were incubated for one hour on ice. Cells were then spun at 400 g in a pre-cooled EPPENDORF™ 581OR centrifuge for five minutes. Supernatants were removed and cells washed with 200 ml of BD™ Facs buffer. Cells were washed twice and then resuspended in 200 ml of FACs buffer. Samples were then analyzed on an LSRII (BD™ biosciences) with DIVA software (BD™ biosciences). CD86 and MHCII geo mean fluorescence was assessed using FLOWJO™ analysis software. A ratio between SEA-h00 and SEA-CD40 was calculated and the fold change used to calculate a range of SEA-CD40 potency.

Results:

Activation of CD40, in addition to eliciting cytokine production, promotes the maturation of antigen presenting cells. DC maturation can be followed by upregulation of activation markers including CD86 and MHCII. Human PBMC cultures were stimulated with SEA CD40 and an SEA-isotype control for 6, 24, or 48 hours and surface expression of MHC Class II antigens (HLA DR, DP, DQ) and CD86 was assessed. SEA-CD40 stimulation, but not the isotype control resulted in a significant increase in both MHCII (Table 4) and CD86 (data not shown) at concentrations as low as 0.01 µg/mL.

TABLE 4

| MHCII | | | |
|---|---|---|---|
| SEA-CD40 | 6 hrs | 24 hrs | 48 hrs |
| 100 | 1.13 | 1.64 | 2.10 |
| 10 | 1.10 | 1.62 | 2.10 |
| 1 | 1.14 | 1.76 | 1.57 |
| 0.1 | 0.90 | 1.19 | 1.50 |
| 0.01 | 0.90 | 1.21 | 1.38 |
| 0.001 | 1.00 | 1.07 | 1.10 |
| 0.0001 | 0.85 | 1.05 | 0.99 |

Figure 7:
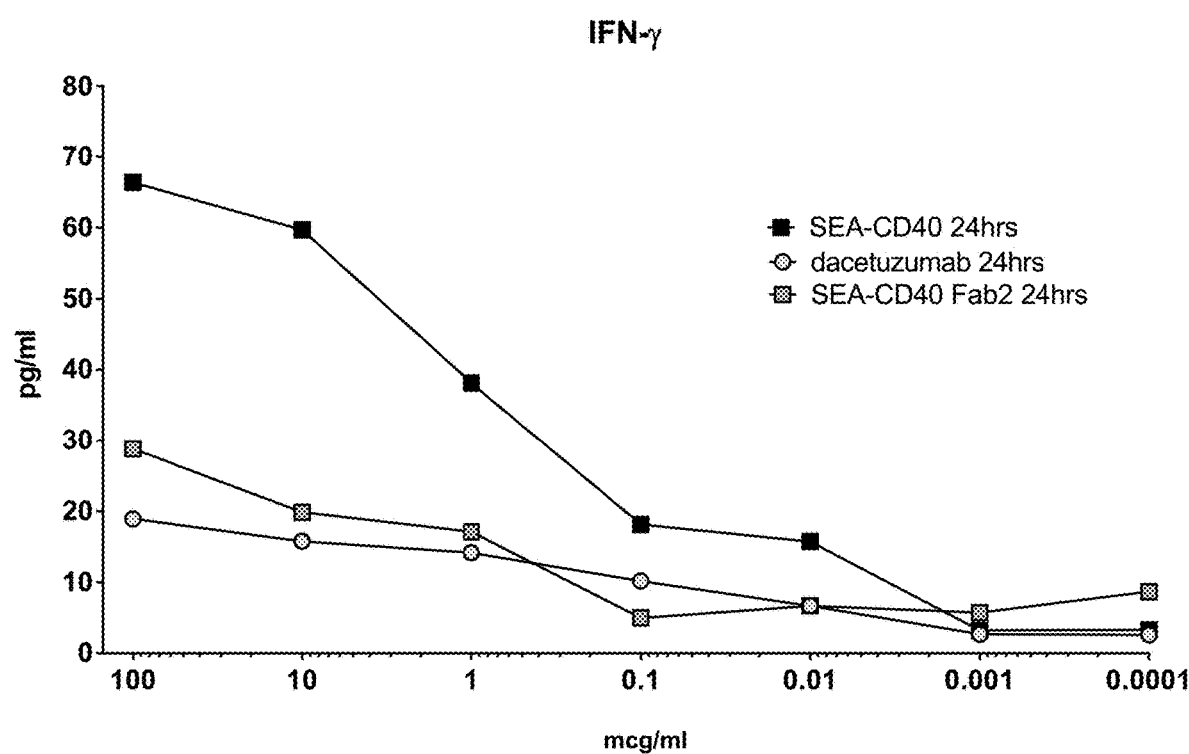
FIG. 7 provides interferon-γ (IFNγ) production by PBMCs as a result of treatment with SEA-CD40 (closed squares); dacetuzumab (grey circles); or SEA-CD40 F(ab')$_2$ (grey squares).

Role of Fucose in Immune Activation by SEA-CD40:

Human PBMCs were isolated as described above. PBMCs were treated with various concentrations of SEA-CD40, the parental antibody SGN40, or a F(ab)'2 version of SEA-CD40 and incubated for 24 hrs. For assessment of B cell depletion, BPMC cultures were stained with a PE-CD19 and B-cell numbers were quantified by flow cytometry. For assessment of cytokine production, PBMC tissue culture supernatants were collected and cytokine production assessed by multiplex analysis on the Luminex platform. IFNγ production is shown is shown in FIG. 7, (ng/mL) and similar trends were seen for the other cytokines. For assessment of antigen presenting cell maturation, PBMC's were collected after the twenty-four hour incubation and stained with aPE-anti-CD86 or APC-pan MHC Class II antigen (DR, DQ, DP) antibody and the percent positive cells were assessed by flow cytometry. The data are shown as mean fluorescent intensity for pan MHC markers.

Figure 6:
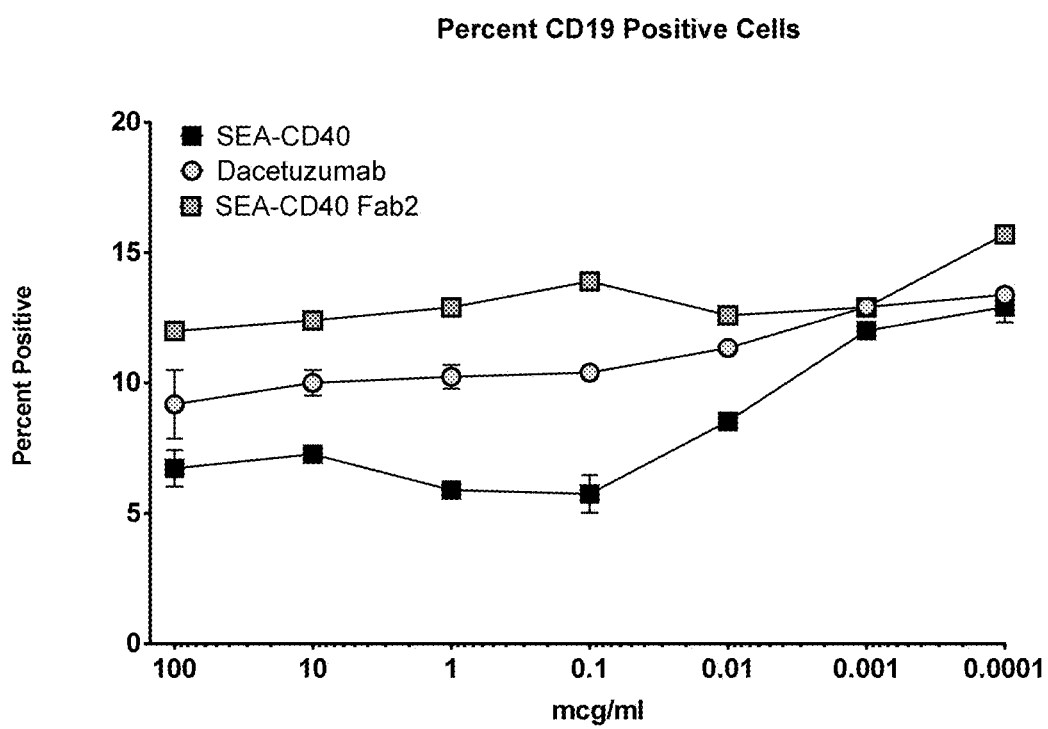
FIG. 6 provides a time course of B-cell depletion from human PBMCs as a result of treatment with SEA-CD40 (closed squares); dacetuzumab (grey circles); or SEA-CD40 F(ab')$_2$ (grey squares).

Results:

To assess B cell depletion, human PBMC cultures were treated with multiple concentrations of SEA-CD40, dacetuzumab, or SEA-CD40 F(ab')2 for twenty-four hours. Results are shown in FIG. 6. The ADCC-mediated depletion of B cells was significantly higher in SEA-CD40-treated cultures compared with dacetuzumab-treated cultures and this activity was lost with the SEA-CD40 F(ab)'2.

Figure 8:
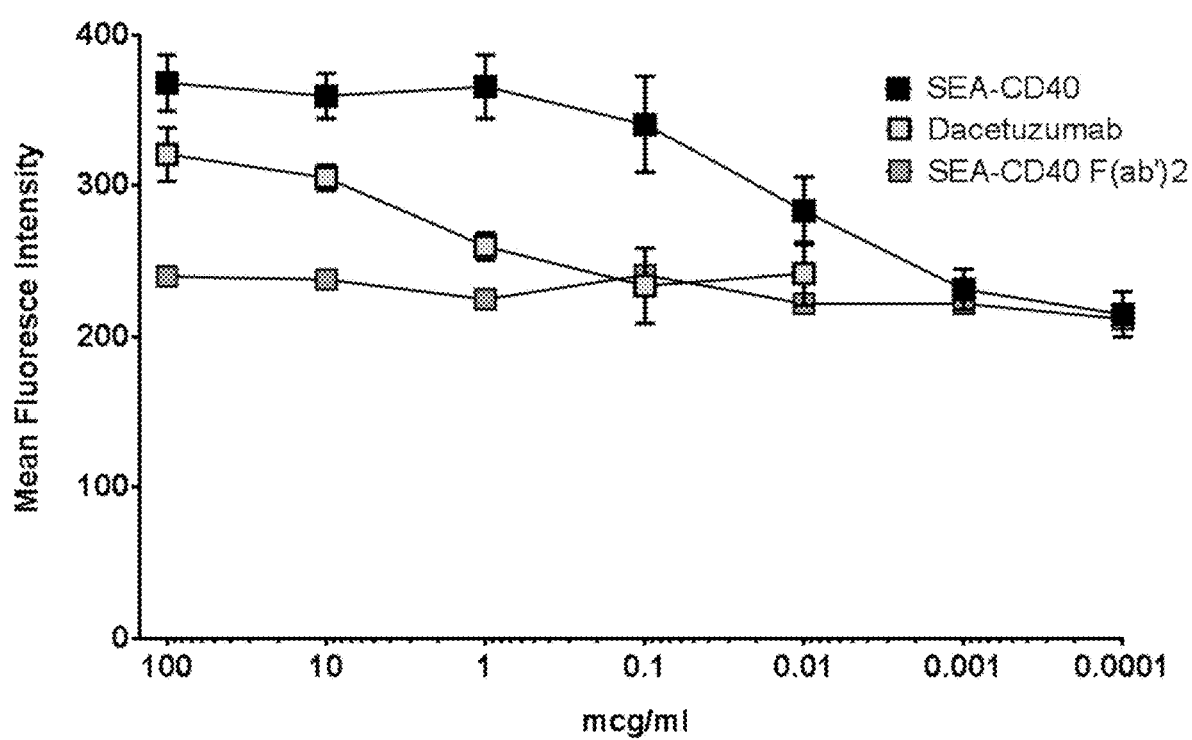
FIG. 8 demonstrates induction of HLA-DR/DQ/DP as a marker for antigen presenting cell maturation by PBMCs as a result of treatment with SEA-CD40 (closed squares); dacetuzumab (grey circles), or SEA-CD40 F(ab')$_2$ (grey squares).

Additionally immune activation endpoints (cytokines and APC activation/maturation markers) were assessed in SEA-CD40, dacetuzumab, and SEA-CD40 F(ab')2 PBMC cultures stimulated for twenty-four hours. SEA-CD40 stimulation of both cytokine production (FIG. 7) and APC maturation (FIG. 8) was significantly higher than that of dacetuzumab or SEA-CD40 F(ab')2. These data demonstrate that the lack of fucose on the IgG domain does not alter CD40 binding, but does increase FcγRIIIa binding resulting in increased CD40 activity and ultimately increased CD40 immune modulatory activity.

Example 3: Immune Modulatory Activity of Non-Fucosylated hS2C6 Antibody

Identification of Active Doses of SEA-CD40:

SEA-CD40 is proposed to be active at dose levels that activate antigen-presenting cells, which can be characterized by upregulation of activation markers, such as MHC class I or II, or CD86. Activation markers on PBMCs following treatment with various concentrations of SEA-CD40 from 6 to 48 hours were assessed as described above (Assessment of Activation markers on PBMCs). The difference between treatments with isotype control SEA-h00 and SEA-CD40 for each activation marker were calculated and plotted versus SEA-CD40 concentrations and treatment time. The steepest response-concentration curves were observed at 24 hours for CD86 and MHCII and 48 hours for MHCI. Response-concentration data (24 hr CD86, 24 hr MHCII and 48 hr MHCI) were fitted by nonlinear regression using the following equation, where 0% and 100% responses are defined as the smallest and largest values in the data set for each activation marker. EC50 is the concentration of SEA-CD40 that gives a 50% response.

$$\text{Response} = \frac{100}{1 + 10^{(\log_{10} EC50 - \log_{10} Concentration)}}$$

Figure 9:
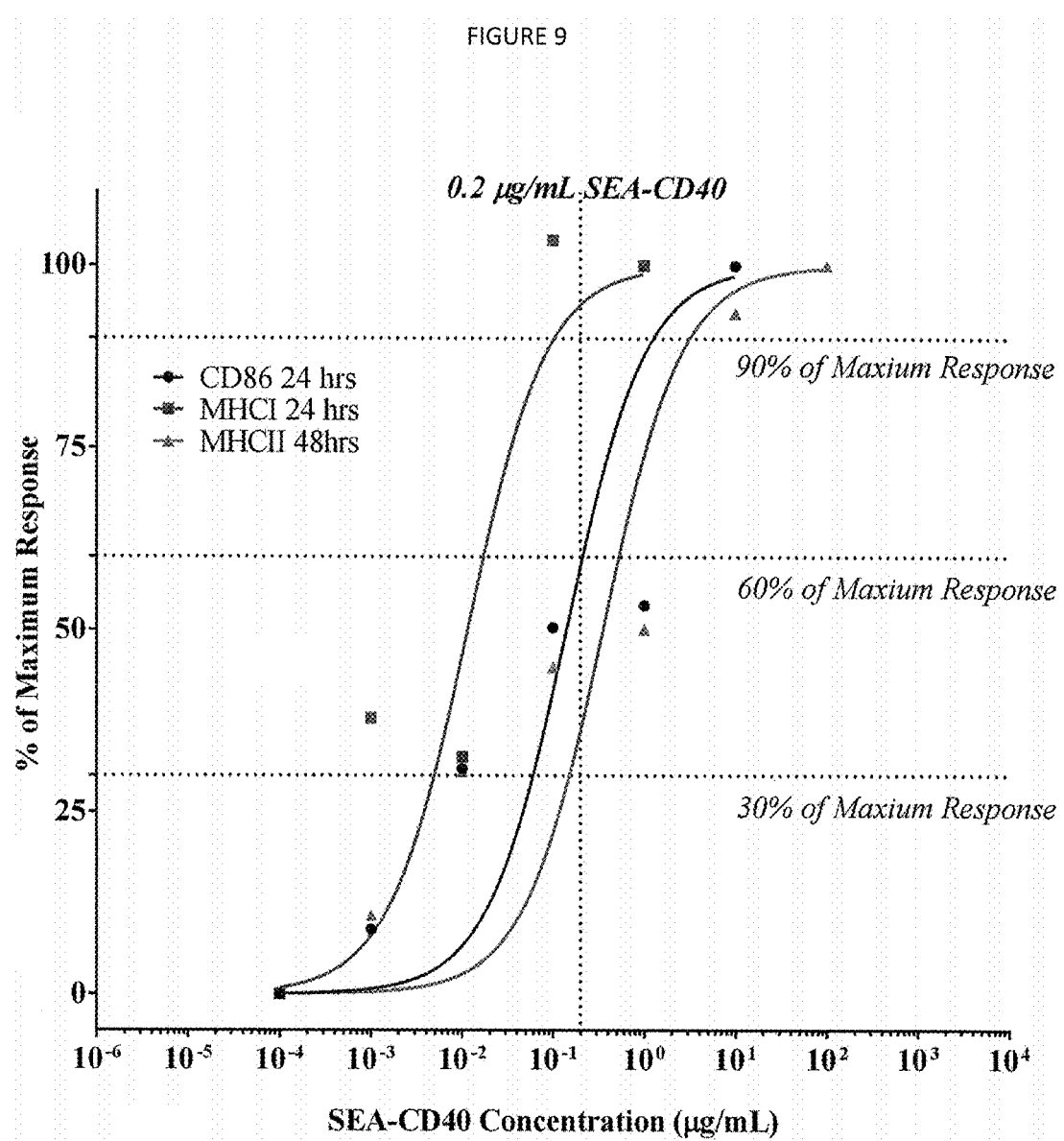
FIG. 9 provides concentration vs. normalized response curves for immune activation markers in PBMCs treated with varying concentration of SEA-CD40.

Results:

Normalized response versus-log (concentration) and non-linear fitted regression lines for activation markers are illustrated in FIG. 9. Estimated EC50 values for MHCI, CD86 and MHCII were 0.011, 0.14 and 0.41 μg/mL, respectively. SEA-CD40 is estimated to induce approximately 90%, 60%, and 30% maximal upregulation of MHCI, CD86 and MHCII, respectively, at 0.2 μg/mL, corresponding to a theoretical plasma Cmax achievable by an IV dose of 10 μg/kg in humans. This dose is proposed as the theoretical first anticipated active dose.

Example 4: Immune Modulatory Activity of Non-Fucosylated hS2C6 Antibody

T-Cell Response Generated by SEA-CD40:

An anti-M1 T cell line was generated at ASTARTE BIOLOGICS™ from a HLA-A2 donor that was shown to be highly reactive to the M1 flu peptide. These cells were labeled with carboxyfluorescein succinimidyl ester (CF SE) and combined with autologous PBMC's. Cultures were stimulated with 10 μg/ml M1 flu peptide in the presence or absence of decreasing concentrations (1, 0.1, 0.01 μg/ml) of SEA-CD40 or dacetuzumab for 5 days. Cultures supernatants were collected and analyzed for cytokines by multiplex analysis on the LUMINEX™ platform and antigen specific T-cells were identified by M1 specific Tetramer binding.

Figure 10A:
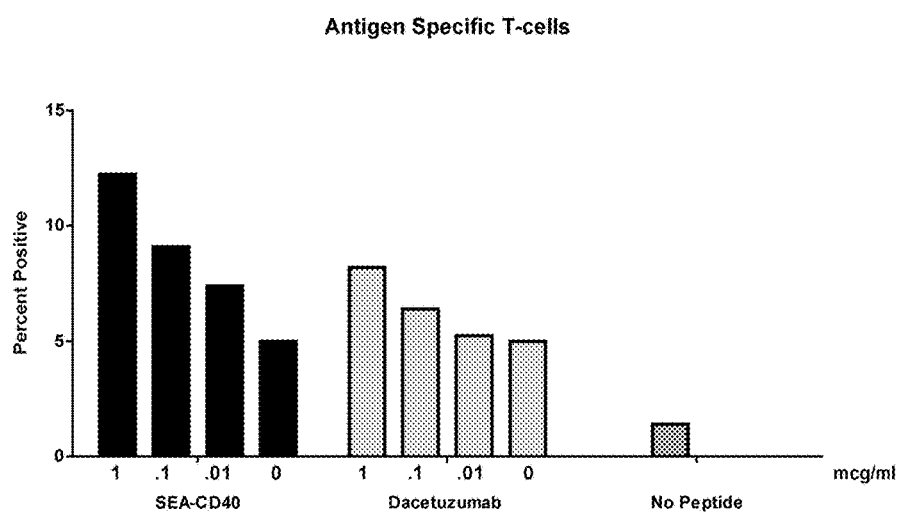
FIGS. 10A and 10B compare the immune response to the M1 flu peptide by PBMCs incubated with SEA-CD40 or dacetuzumab.
Figure 10B:
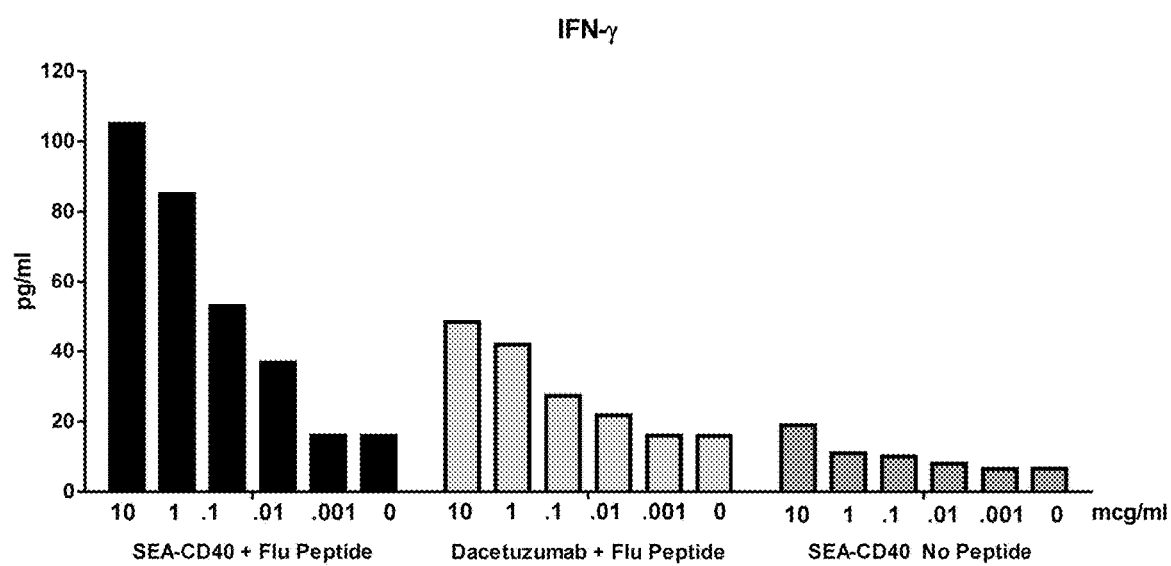

Results:

PBMC's from an HLA-A2 donor shown to be highly reactive to the M1 flu peptide were stimulated with M1 flu peptide in the presence or absence of decreasing concentrations of SEA-CD40 or dacetuzumab for five days. Results are shown in FIGS. 10A and 10B. SEA-CD40 stimulated cultures showed increased response to M1 flu antigen as seen by an increase in IFNγ production and an increase in antigen specific T-cells as determined by increased Tetramer binding. SEA-CD40 stimulated an antigen specific T-cell response down to 0.1 ug/ml and this activity was more robust than the response associated with dacetuzumab.

T-Cell Response Generated by SEA-CD40 in Combination with Anti-Immune Checkpoint Inhibitor Antibodies:

An anti-M1 T cell line was generated at ASTARTE BIOLOGICS™ from a HLA-A2 donor that was shown to be highly reactive to the M1 flu peptide. These cells were labeled with CFSE and combined with autologous PBMC's. Cultures were stimulated with 10 ug/ml M1 flu peptide in the presence or absence of decreasing concentrations (1, 0.1, 0.01 ug/ml) of SEA-CD40 and/or 1 ug/ml of an anti-CTLA4 or an anti-PD-1 antibody for five days. Culture supernatants were collected and analyzed for cytokines by multiplex analysis on the LUMINEX™ platform and antigen specific T-cells were identified by M1 specific Tetramer binding.

Figure 11:
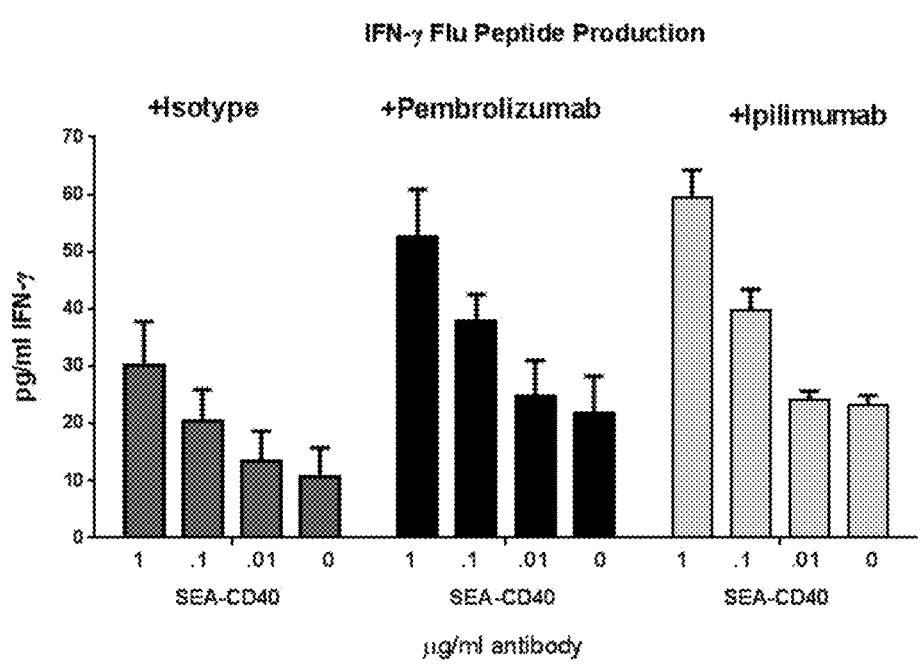
FIG. 11 demonstrates enhancement of the immune response to the M1 flu peptide by PBMCs incubated with a combination of SEA-CD40 and either an anti-CTLA-4 antibody or an anti-PD-1 antibody. IFNγ levels are shown in FIG. 11.
Figure 12:
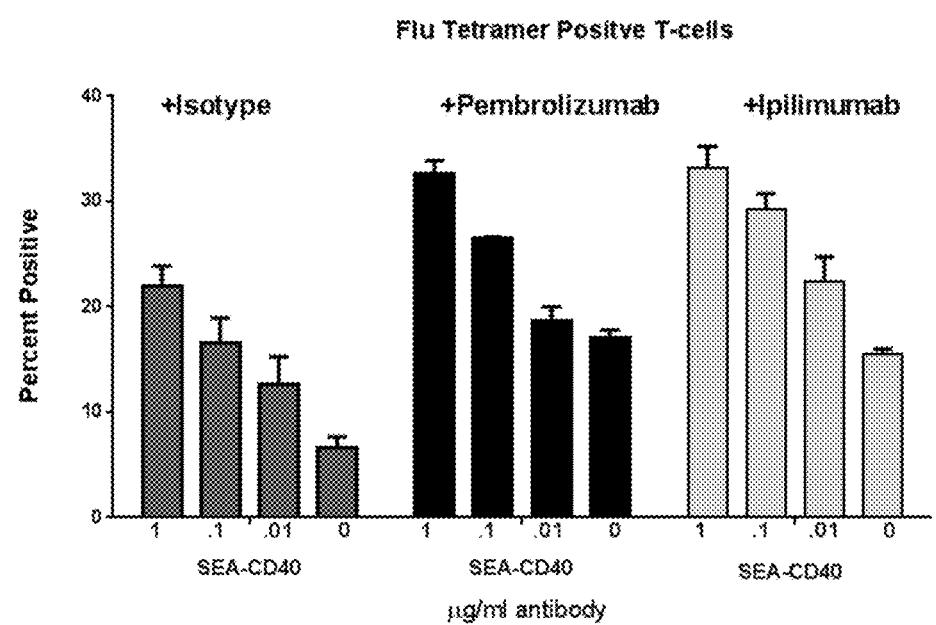
FIG. 12 demonstrates enhancement of the immune response to the M1 flu peptide by PBMCs incubated with a combination of SEA-CD40 and either an anti-CTLA-4 antibody or an anti-PD-1 antibody. Levels of antigen specific T cells are shown in FIG. 12.

Results:

PBMC's from an HLA-A2 donor shown to be highly reactive to the M1 flu peptide were stimulated with M1 flu peptide in the presence or absence of decreasing concentrations of SEA-CD40 and/or a constant concentration of an anti-CTLA4 blocking antibody or an anti-PD-1 antibody. Results are shown in FIGS. 11 and 12. While SEA-CD40, anti-CTLA4 antibodies and anti-PD-1 antibodies alone stimulated an antigen specific T-cell response, increased response to M1 flu antigen as seen by an increase in IFN-γ production (FIG. 11) and an increase in antigen specific T-cells as determined by increased Tetramer binding (FIG. 12, using the Tetramer/APC—HLA-A*02:01 Influenza-M1 (GILGFVFTL) tetramer from MBL) was observed when SEA-CD40 and anti-CTLA4 antibodies or anti-PD-1 antibodies were combined. SEA-CD40 stimulated an antigen specific T-cell response down to 0.1 ug/ml and this activity was enhanced by combination with an immune checkpoint antibody.

T-Cell Response Generated by SEA-CD40 in PCMCs from Cancer Patients:

For assessment of anti-CD40 antibodies alone, PBMCs were isolated from 10 mls of tumor patient blood and 0.25 million cells were plated in a 24 well plate. Samples were treated with increasing concentrations of SEA-CD40 only, or 1 ug/ml of a combined peptide pool containing MageA1/MageA3/NY-ESO and increasing concentration of either SEA-CD40 or SGN-40. Samples were cultured in 10% $CO_2$ at 37° C. for five days, tissue culture supernatants were collected and INF-γ levels were assessed.

For assessment of SEA-CD40 in combination with immune checkpoint blocking antibodies, PBMCs were isolated from 10 mls of blood from patients diagnosed with either breast, pancreatic, of melanoma cancer, and 0.25 million cells were plated in a 24 well plate. Samples were treated with increasing concentrations of SEA-CD40, 1 μg/ml of a combined peptide pool containing MageA1/MageA3/NY-ESO, and either 1 μg/ml of anti-PD1 or anti-CTLA4. Samples were cultured in 10% $CO_2$ at 37° C. for 5 days, tissue culture supernatants were collected and INF-γ levels were assessed.

Figure 13:
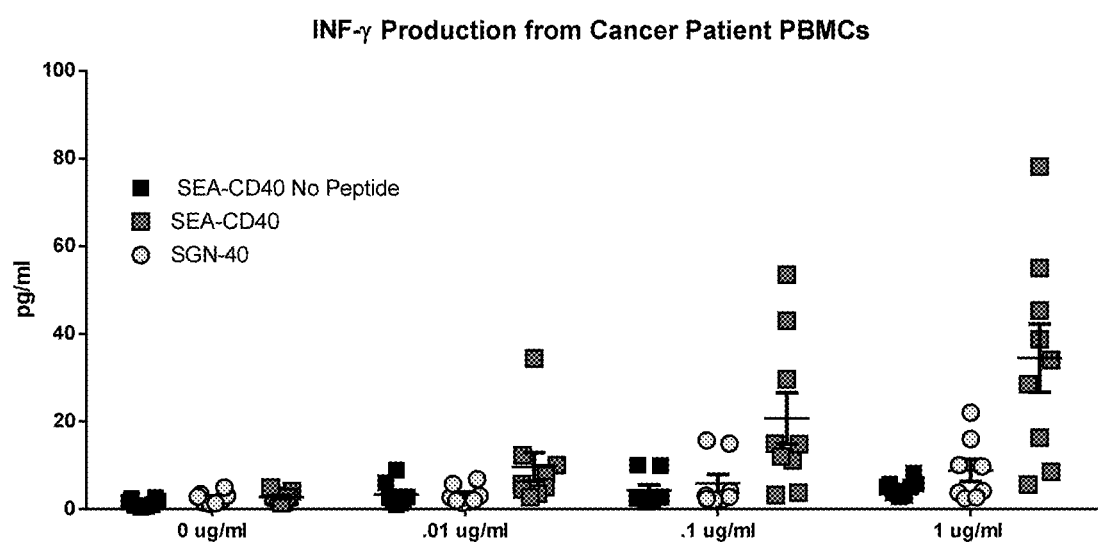
FIG. 13 provides the immune response (IFNγ production) of PBMCs from donors with cancer to common tumor antigen peptides (MAGEA1/MAGE3/NY-ESO). PBMC's were incubated in the presence or absence of increasing concentrations of SEA-CD40 or SGN-40 for 5 days.

Results:

PBMC's from donors were isolated from whole blood as described above. The donors were three patients diagnosed with melanoma, three patients diagnosed with breast cancer, and three patients diagnosed with pancreatic cancer. Donor PBMC's were stimulated with a pool of peptides of the common tumor antigen proteins (MAGEA1/MAGE3/NY-ESO) in the presence or absence of increasing concentrations of SEA-CD40 or SGN-40 for 5 days. Tissue culture supernatants were collected and INF-γ production was assessed. Results are shown in FIG. 13. Six out of the nine patients exhibited an antigen dependent INF-γ response that was significantly enhanced by SEA-CD40 treatment as compared to treatment with SGN-40. In the SEA-CD40 treated PBMC's, stimulation was observed at concentrations as low as 10 μg/ml.

Figure 14:
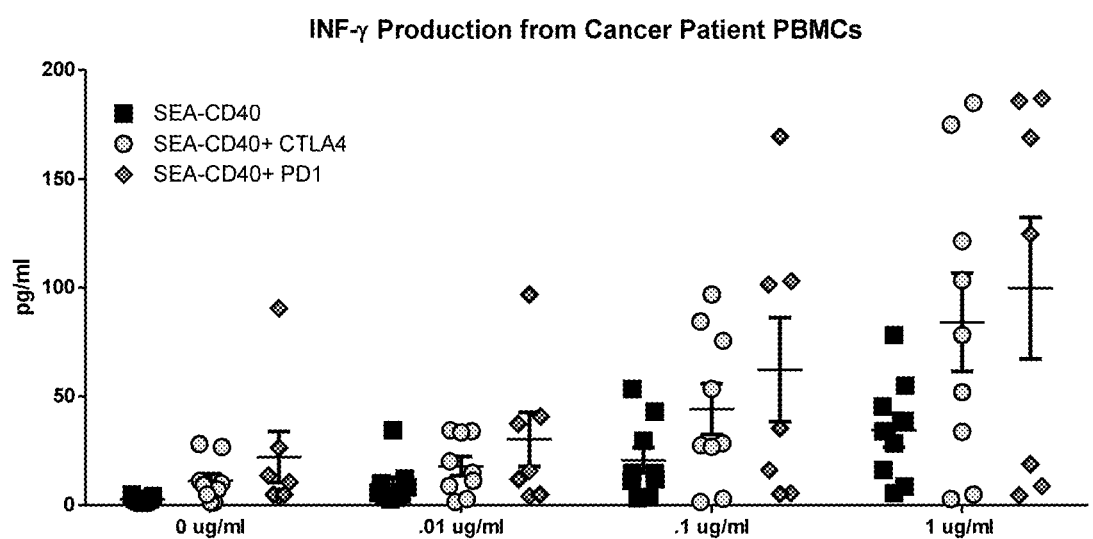
FIG. 14 provides the immune response (IFNγ production) of PBMCs from donors with cancer to common tumor antigen peptides (MAGEA1/MAGE3/NY-ESO). PBMC's were incubated in the presence or absence of increasing concentrations of SEA-CD40 and/or a constant concentration of an anti-CTLA4 or anti-PD1 blocking antibody.

PBMC's from donors were isolated from whole blood as described above. As above, the donors were three patients diagnosed with melanoma, three patients diagnosed with breast cancer, and three patients diagnosed with pancreatic cancer. Donor PBMC's were stimulated with a pool of peptides of the common tumor antigen proteins (MAGEA1/MAGE3/NY-ESO) in the presence or absence of increasing concentrations of SEA-CD40 and/or a constant concentration of an anti-CTLA4 or anti-PD1 blocking antibody. Results are shown in FIG. 14. While SEA-CD40 and antibodies against the checkpoint blockade targets PD1 and CTLA4 stimulated an antigen specific T-cell response alone, a robust signal to the tumor antigen as measured by INF-γ production was observed when SEA-CD40 was combined with either anti-CTLA4 antibodies or anti-PD1 antibodies.

Example 5: Mouse Models for Activity of Non-Fucosylated Anti-CD40 Antibodies

Mouse models have been proven to be very useful in assessing efficacy and mechanisms of new cancer therapeutics. Study of SEA-CD40 in mouse models of cancer has been difficult because SEA-CD40 does not recognize murine CD40. Therefore, to assess the activity of the non-fucosylated anti-CD40 antibodies a syngeneic murine tumor model was developed. The murine functional equivalents of human IgG1 and human FcγRIII/CD16 are murine IgG2a and FcγRIV, respectively, and binding of murine IgG2a to murine FcγRIV mediates ADCC. See, e.g., Bruhns, *Blood* 119:5640-5649 (2012) and Nimmeriahn et al., *Immunity* 23:41-51 (2005). The rat antibody 1C 10 was used to generate a surrogate of SEA-CD40. See, e.g., Heath et al., *Eur. J. Immunol.* 24:1828-1834 (1994). Briefly, the VL and VH gene fragments of a rat monoclonal antibody that recognizes murine CD40, the 1C10 antibody were cloned in-frame 5' to murine Ckappa and murine IgG2a CH1-CH2-CH3 fragments, respectively. Expression of the resulting genes in CHO cells generated a chimeric 1C10 antibody with rat VL and VH domains and murine light and heavy chain domains of the IgG2a isotype (mIgG2a 1C10). mIgG2a 1C10 was expressed in the presence of 2-fluorofucose in the CHO cell growth medium using the methods described in Example 1, to generate a non-fucosylated form of mIgG2a 1C10 (mIgG2a SEA 1C10). Fucosylated mIgG2a 1C10 and mIgG2a SEA 1C10 were tested for anti-tumor activity using a mouse B16 melanoma model.

Assessment of Non-Fucosylated Murine Antibody Binding to Murine Fcγ Receptors:

CHO cells stably expressing murine FcγRI or FcγRIV were incubated with increasing concentrations of fucosylated mIgG2a 1C10 or non-fucosylated mIgG2a 1C10 (mIgG2a SEA-1C10). Samples were washed and a saturating amount of PE-anti-mouse IgG was added and incubated with the samples on ice for thirty minutes. Samples were washed again and labeled cells were analyzed by flow cytometry.

Figure 15A:
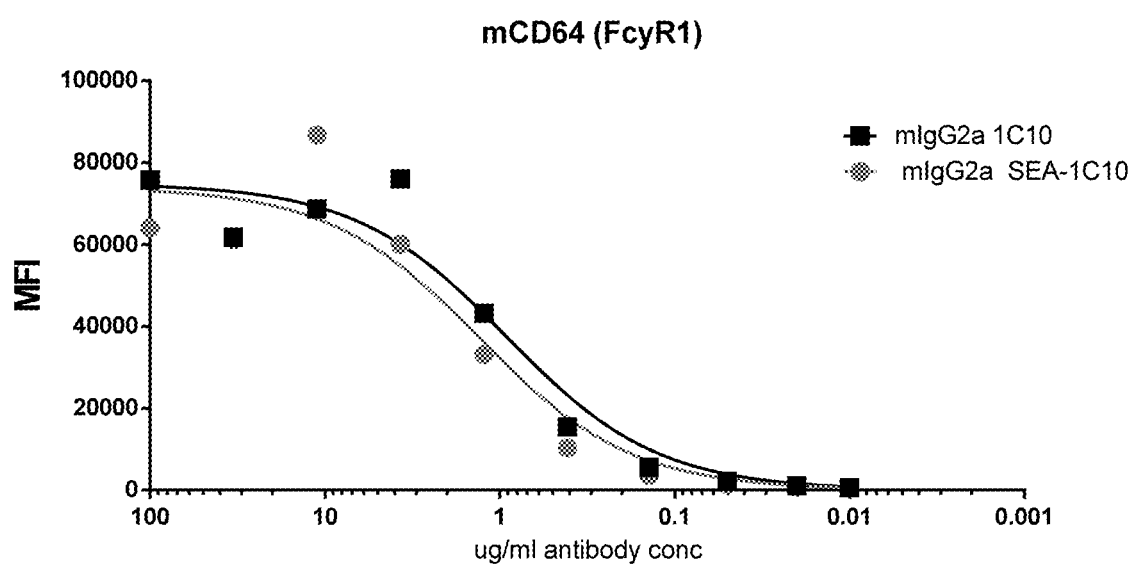

Results:

Binding of the surrogate anti-CD40 antibodies to Chinese hamster ovary (CHO) cells expressing the murine FcγRI or FcγRIV (the murine equivalent to human FcγRIII/CD16) was assessed. Results are show in FIGS. 15A and 15B. As expected mIgG2a 1C10 bound with similar affinity as mIgG2a SEA 1C10 to FcγR1. See, e.g., FIG. 15A. However, non-fucosylated mIgG2a SEA 1C10 bound to FcγRIV at significantly higher affinity than the fucosylated parental antibody mIgG2a 1C10. See, e.g., FIG. 15B.

Assessment of Non-Fucosylated Anti-CD40 Antibodies in a Murine Tumor Model:

250.0E+3 B16F10 melanoma cells were given subcutaneously to C57BL/6 mice. Mice were randomized into cohorts each with tumor size of approximately 50 mm³ on average. Mice were then given interperitoneal injections of either an isotype control (mIgG2a), fucosylated mIgG2a 1C10, or non-fucosylated mIgG2a 1C10 (mIgG2a SEA 1C10), every other day for a total of three doses. Mice were monitored until the tumor size reached 1000 mm³, at which point the mice were sacrificed.

Figure 16:
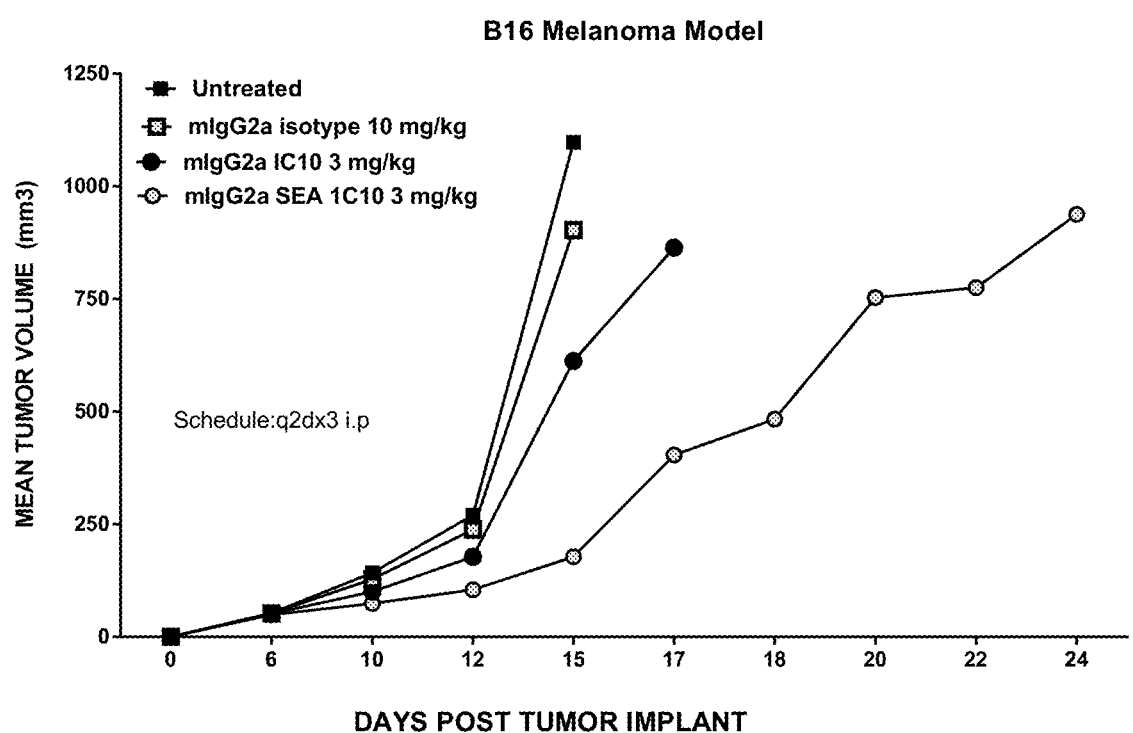
FIG. 16 demonstrates in vivo activity of fucosylated and non-fucosylated anti-CD40 antibody surrogates in the mouse B16 melanoma model.

Results:

The B16F10 syngeneic melanoma model was used to assess the in vivo efficacy of our non-fucosylated anti-CD40 antibody surrogates. C57BL/6 mice were implanted with B16F10 melanoma cells, and then treated with either mIgG2a isotype control, fucosylated mIgG2a 1C10, or non-fucosylated mIgG2a 1C10 (mIgG2a SEA 1C10). Tumor burden was monitored and mice were sacrificed when the tumor size reached 1000 mm³. Results are shown in FIG. 16. Mice treated with non-fucosylated SEA-1C10 mIgG2a showed a significant survival benefit and tumor delay compared to the fucosylated parent 1C10 IgG2a antibody.

Example 6: SEA-CD40 Depletes B-Cells and Promotes T-Cell Activation

SEA-CD40 activity was compared to a related fucosylated antibody and to a fully agonistic anti-CD40 antibody, clone 21.4.1. Antibody 21.4.1 is a human anti-CD40 IgG2k agonistic antibody that is the parent clone of CP-870,893, an antibody that is currently being tested in a clinical trial of solid tumors in combination with PDL1. For amino acid sequence information for antibody 21.4.1, see, e.g., U.S. Pat. No. 7,338,660, which is herein incorporated for all purposes. Three functional areas were tested for the antibodies: ability to drive human B-cells differentiation, activation, and depletion, ability to activate primary human PBMC cultures, and ability to drive an antigen specific response.

Assessment of B-Cell Activation by Anti-CD-40 Antibodies:

Experiments were performed using purified B-cells from fresh human whole blood or human peripheral blood mononuclear cells (PBMCs). B-cells were isolated from fresh human whole blood using ROSETTESEP™ isolation kit. The isolated, purified B-cells were cultured with increasing concentrations of SEA-CD40, antibody 21.4.1, or hexameric CD40 ligand, ENZO LIFE SCIENCES™ (10, 1, 0.1, 0.01, or 0.001 µg/mL) for 24 hours. B-cell activation was assessed as upregulation of CD80 by Flow Cytometry.

PBMCs were isolated as described above and were then cultured with increasing concentrations of SEA-CD40, antibody 21.4.1, or hexameric CD40L (10, 1, 0.1, 0.01, or 0.001 µg/mL) for 24 hours. The total number of B-cells assessed with CD19 staining assessed by flow cytometry.

Figure 17:
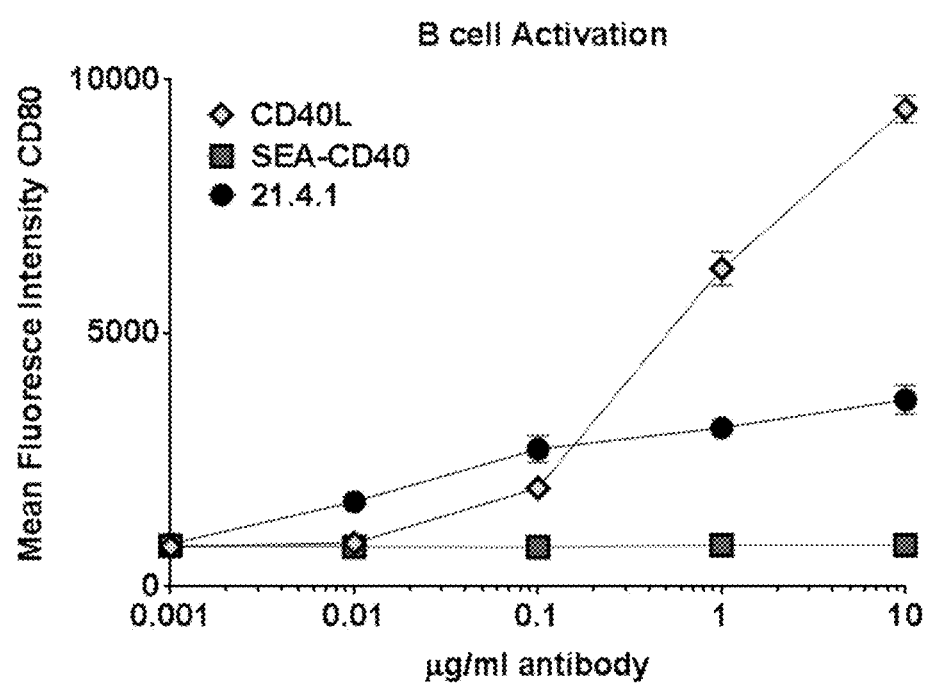
FIG. 17 demonstrates B-cell activation activity of SEA-CD40, antibody 21.4.1, and CD40 hexameric ligand. Experiments were performed using purified B-cell cultures.

Results:

SEA-CD40 immune modulatory activity is dependent on the Fc portion of the antibody and its interaction with the CD16, the FcγRIII receptor. Results are shown in FIG. 17. SEA-CD40 does not induce B-cell activation in purified B-cells cultures which lack cells that express the Fcγ receptors needed for crosslinking of SEA-CD40. This differs from the CD40 activating antibody 21.4.1 which is able to drive B-cell activation in pure B-cell cultures similar to CD40 ligand.

Figure 18:
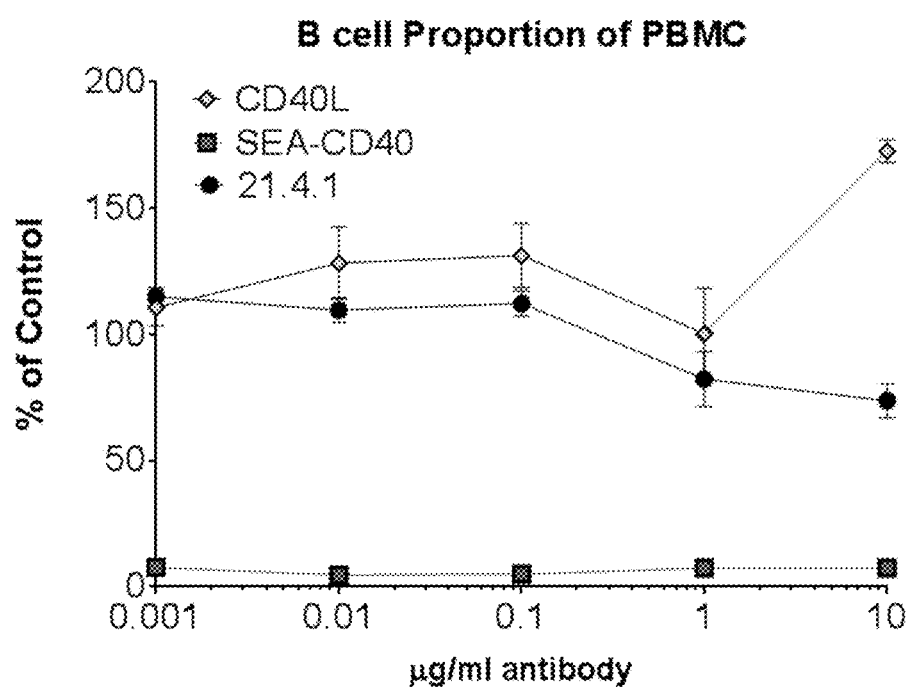
FIG. 18 demonstrates B-cell activation activity of SEA-CD40, antibody 21.4.1, and CD40 hexameric ligand. Experiments were performed using PBMC cultures.

PBMCs include cells that express the Fcγ receptors. Results for that cell population are shown in FIG. 18. For PBMC cultures, SEA-CD40 was able to promote ADCC depletion of B-cells, while antibody 21.4.1 treatment did not deplete B-cells.

Assessment of Monocyte/Macrophage Activation by Anti-CD-40 Antibodies:

Human PBMC cultures were isolated as described above. PBMC cultures were stimulated with increasing concentrations (0.0, 0.001, 0.01, 0.1, 1.0, or 10 µg/mL) of SEA-CD40, dacetuzumab, antibody 21.4.1, or an SEA-isotype control for twenty-four hours. Upregulation of CD80 is a marker of monocyte maturation. Surface expression of CD80 was assessed by flow cytometry.

Figure 19:
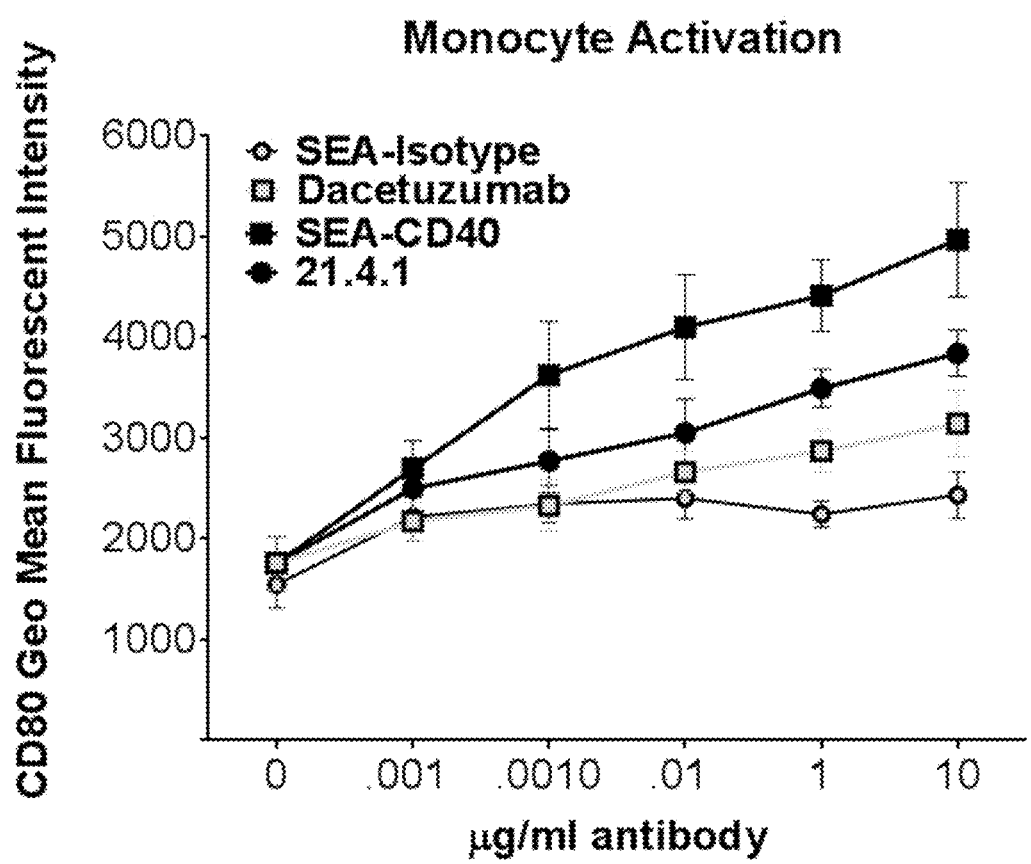
FIG. 19 demonstrates monocyte/macrophage activation activity of SEA-CD40, antibody 21.4.1, dacetuzumab and an SEA-isotype control.

Results:

Results are shown in FIG. 19. SEA-CD40 treatment of PBMCs induces robust activation of monocyte/macrophages as measured by CD80 up-regulation and this activity is on par with the activation seen with the CD40 activating antibody 21.4.1.

Assessment of Cytokine Induction by Anti-CD40 Antibodies:

Human PBMC cultures were isolated as described above. PBMC cultures were stimulated with increasing concentrations (0.0, 0.001, 0.01, 0.1, 1.0, or 10 µg/mL) of SEA-CD40, dacetuzumab, antibody 21.4.1, or an SEA-isotype control for twenty-four hours. Following stimulation, tissue culture supernatants were collected and inflammatory cytokines assessed by multiplexed LUMINEX™ analysis.

Figure 20:
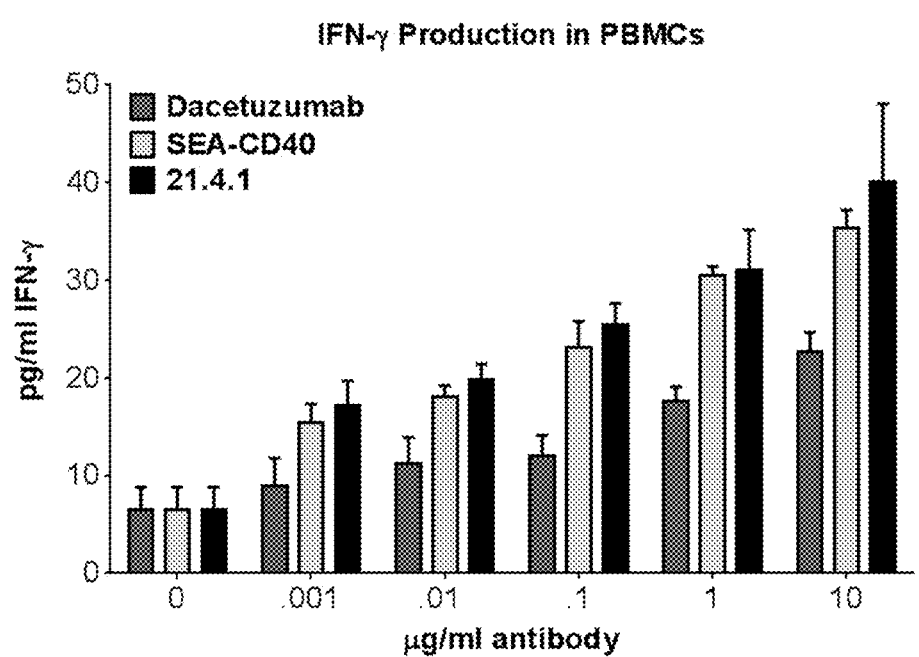
FIG. 20 demonstrates induction of interferon-γ (IFN-γ) levels by SEA-CD40, antibody 21.4.1, dacetuzumab or an SEA-isotype control.
Figure 21:
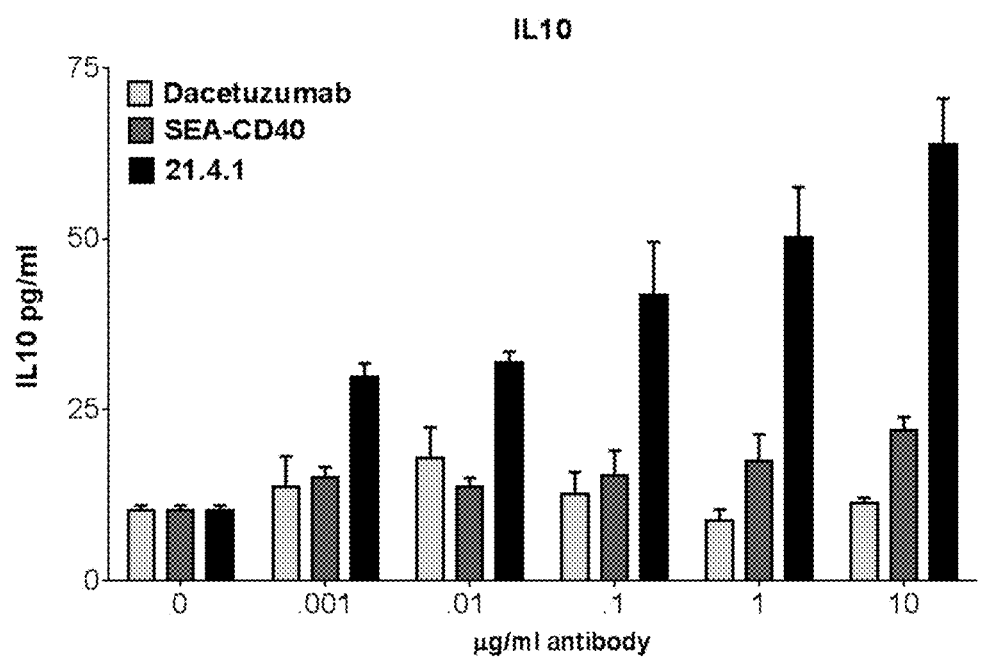
FIG. 21 demonstrates induction of interleukin 10 (IL10) levels by SEA-CD40, antibody 21.4.1, dacetuzumab or an SEA-isotype control.

Results:

Results are shown in FIG. 20 and FIG. 21. FIG. 20 shows that SEA-CD40 and the CD40 activating antibody 21.4.1 induce cytokines IFN-γ and chemokines important for eliciting robust T-cell responses. FIG. 21 shows the induction of interleukin 10 (IL10) by the antibodies. In contrast to antibody 21.4.1, which promotes IL10 production, SEA-CD40 reduces the levels of the immune dampening cytokine IL-10.

Assessment of T-Cell Induction by Anti-CD40 Antibodies:

Human PBMC cultures were isolated as described above. $1 \times 10^6$ PBMCs were cultured in DMEM+10% FBS and incubated with 5 ug of M1 flu peptide, and with increasing concentrations (0.0, 0.001, 0.01, 0.1, 1.0, or 10 µg/mL) of SEA-CD40, dacetuzumab, or antibody 21.4.1 for five days. Cells and cell culture supernatants were then collected. IFN-γ levels were assessed in supernatants. Flu antigen-specific T-cells assessed by tetramer staining using by flow cytometry. Percent T-regulatory cells, a CD4+, CD25+, CD127 low population of cells was determined using flow cytometry.

Figure 22:
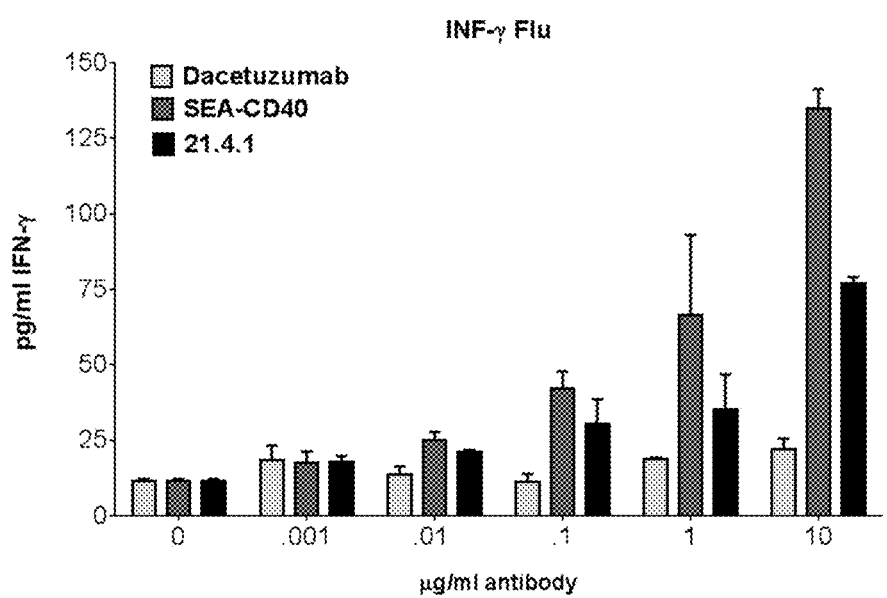
FIG. 22 demonstrates induction of interferon-γ (IFN-γ) levels by SEA-CD40, antibody 21.4.1, or dacetuzumab. Incubation was done in the presence of flu peptide.
Figure 23:
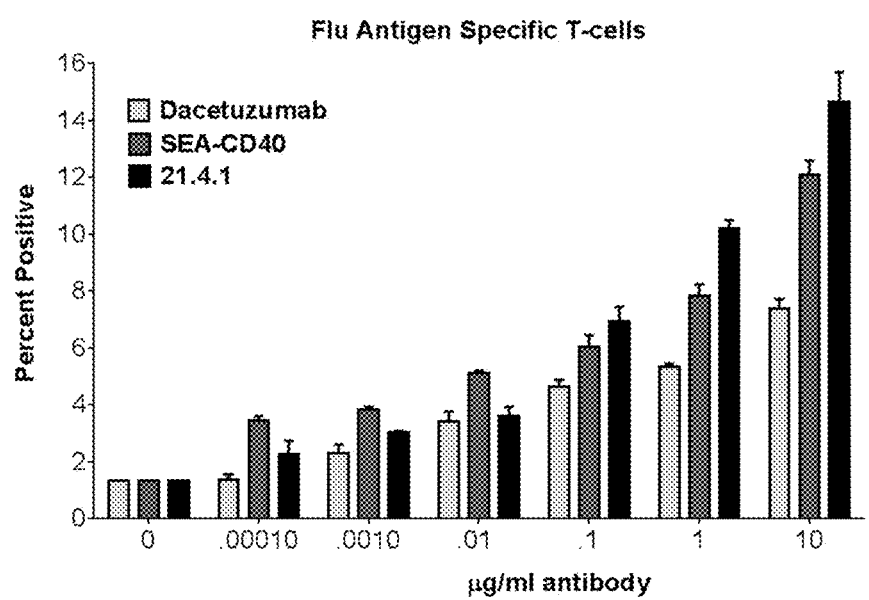
FIG. 23 demonstrates induction a flu-antigen specific T-cell response by SEA-CD40, antibody 21.4.1, or dacetuzumab.
Figure 24:
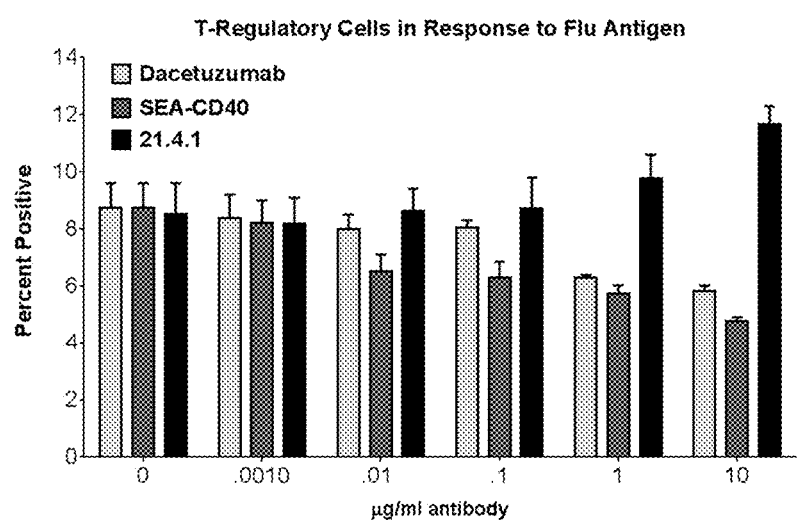
FIG. 24 demonstrates changes in IL10 levels following incubation of PBMCs with flu peptide and SEA-CD40, antibody 21.4.1, or dacetuzumab.

Results:

Results are shown in FIGS. 22-24. After the five day incubation, SEA-CD40 induced higher levels of IFN-γ, as compared to dacetuzumab or antibody 21.4.1, see, e.g., FIG. 22. FIG. 23 shows that SEA-CD40 induces a robust flu antigen specific T-cell response, similar to that seen with antibody 21.4.1. However, FIG. 24 shows that SEA-CD40 also reduces the number of immune inhibitory T-regulatory cells present after flu peptide stimulation. This activity is likely related to the decreased IL10 production seen after treatment of PBMCs with SEA-CD40. In contrast, after incubation with antibody 21.4.1, PBMCs showed increased numbers of T-regulatory cells, as demonstrated in FIG. 24.

Example 7: Administration of SEA-CD40 to Human Cancer Patients

SEA-CD40 is administered to patients with metastatic or unresectable solid tumor malignancy. The SEA-CD40 is administered intravenously at 30 µg/kg on days 1 and 8 of a three-week cycle for two cycles. In subsequent cycles, SEA-CD40 is administered intravenously at 30 µg/kg on day 1 of the three week cycle. Administration of SEA-CD40 continues as directed by a physician so long as patient benefit is present.

SEA-CD40 is administered to patients with advanced hematogical malignancy, e.g., relapsed or refractory Hodgkin lymphoma, diffuse large B-cell lymphoma, or indolent lymphoma, including follicular lymphoma. The SEA-CD40 is administered intravenously at 30 µg/kg on days 1 and 8 of a three-week cycle for two cycles. In subsequent cycles, SEA-CD40 is administered intravenously at 30 µg/kg on day 1 of the three week cycle. Administration of SEA-CD40 continues as directed by a physician so long as patient benefit is present.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

SEQ ID NO: 1; hS2C6 heavy chain
EVQLVESGGGLVQPGGSLRLSCAASGYSFTGYYTHWVRQAPGKGLEWVARVIPNAGGTSY

```
        70        80        90       100       110       120
         |         |         |         |         |         |
NQKFKGRFTLSVDNSKNTAYLQMNSLRAEDTAVYYCAREGIYWWGQGTLVTVSSASTKGP 130       140       150       160       170       180
         |         |         |         |         |         |
SVFPLAPSSKSTSGGTAALGCLVKDYFPEPVTVSWNSGALTSGVHTFPAVLQSSGLYSLS 190       200       210       220       230       240
         |         |         |         |         |         |
SVVTVPSSSLGTQTYICNVNHKPSNTKVDKKVEPKSCDKTHTCPPCPAPELLGGPSVFLF 250       260       270       280       290       300
         |         |         |         |         |         |
PPKPKDTLMISRTPEVTCVVVDVSHEDPEVKFNWYVDGVEVHNAKTKPREEQYNSTYRVV 310       320       330       340       350       360
         |         |         |         |         |         |
SVLTVLHQDWLNGKEYKCKVSNKALPAPIEKTISKAKGQPREPQVYTLPPSREEMTKNQV 370       380       390       400       410       420
         |         |         |         |         |         |
SLTCLVKGFYPSDIAVEWESNGQPENNYKTTPPVLDSDGSFFLYSKLTVDKSRWQQGNVF 430       440
         |         |
SCSVMHEALHNHYTQKSLSLSPGK
```

SEQ ID NO: 2, hS2C6 light chain
DIQMTQSPSSLSASVGDRVTITCRSSQSLVHSNGNTFLHWYQQKPGKAPKLLIYTVSNRF

```
        70        80        90       100       110       120
         |         |         |         |         |         |
SGVPSRFSGSGSGTDFTLTISSLQPEDFATYFCSQTTHVPWTFGQGTKVEIKRTVAAPSV 130       140       150       160       170       180
         |         |         |         |         |         |
FIFPPSDEQLKSGTASVVCLLNNEYPREAKVQWKVDNALQSGNSQESVTEQDSKDSTYSL 190       200       210
         |         |         |
SSTLTLSKADYEKHKVYACEVTHQGLSSPVTKSFNRGEC
```

---

What is claimed is:

1. A method of treating cancer, the method comprising administering a composition comprising an anti-CD40 antibody to a patient in need thereof, wherein the anti-CD40 antibody comprises a heavy chain variable region comprising amino acids 1-113 of SEQ ID NO:1 and a light chain variable region comprising amino acids 1-113 of SEQ ID NO:2, and a human constant region;
wherein the constant region has an N-glycoside-linked sugar chain at residue N297 according to the EU index; and
wherein less than 5% of N-glycoside-linked sugar chains in the composition comprise a fucose residue; and
   wherein the anti-CD40 antibody is administered at a dose level between 2-50 µg/kg (µg per kilogram of patient body weight).

2. The method of claim 1, wherein the patient has a CD40 positive cancer.

3. The method of claim 1, wherein the patient has a CD40 negative cancer.

4. A method of treating cancer, the method comprising administering an anti-PD-1 antibody and a composition comprising an anti-CD40 antibody to a patient in need thereof, wherein the anti-PD-1 antibody is nivolumab or pembrolizumab,
   wherein the anti-CD40 antibody comprises a heavy chain variable region comprising amino acids 1-113 of SEQ ID NO:1 and a light chain variable region comprising amino acids 1-113 of SEQ ID NO:2, and a human constant region;
   wherein the constant region has an N-glycoside-linked sugar chain at residue N297 according to the EU index; wherein less than 5% of N-glycoside-linked sugar chains in the composition comprise a fucose residue; and wherein the anti-CD40 antibody is administered at a dose level between 2-50 µg/kg (µg per kilogram of patient body weight).

5. The method of claim 1, wherein the cancer is a hematologic cancer.

6. The method of claim 1, wherein the cancer is a solid tumor.

7. A method of treating cancer, the method comprising administering a composition comprising an anti-CD40 antibody to a patient in need thereof,
   wherein the anti-CD40 antibody comprises a heavy chain variable region comprising amino acids 1-113 of SEQ ID NO:1 and a light chain variable region comprising amino acids 1-113 comprising amino acids 1-113 of SEQ ID NO:2, and a human constant region;
wherein the constant region has an N-glycoside-linked sugar chain at residue N297 according to the EU index; and wherein less than 5% of N-glycoside-linked sugar chains in the composition comprise a fucose residue; and
   wherein the anti-CD40 antibody is administered at a dose level of 30 µg/kg (µg per kilogram of patient body weight).

8. The method of claim 7, wherein the anti-CD40 antibody is administered at least once every three weeks.

9. The method of claim 8, wherein the anti-CD40 antibody is administered on day one of a three week cycle.

10. The method of claim 8, wherein the anti-CD40 antibody is administered on days one and eight of a three week cycle.

11. The method of claim 7, wherein the patient has a CD40 positive cancer.

12. The method of claim 7, wherein the patient has a CD40 negative cancer.

13. The method of claim 1, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

14. The method of claim 13, wherein the cancer is pancreatic cancer.

15. The method of claim 4, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

16. The method of claim 4, wherein the anti-PD-1 antibody is pembrolizumab.

17. The method of claim 4, wherein the cancer is pancreatic cancer, and the anti-PD-1 antibody is pembrolizumab.

18. The method of claim 7, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

19. The method of claim 18, wherein the cancer is pancreatic cancer.

20. The method of claim 7, further comprising administering an anti-PD-1 antibody to the patient, wherein the anti-PD-1 antibody is nivolumab or pembrolizumab.

21. The method of claim 20, wherein the cancer is pancreatic cancer.

22. The method of claim 20, wherein the cancer is pancreatic cancer, and the anti-PD-1 antibody is pembrolizumab.

23. The method of claim 1, wherein the anti-CD40 antibody is administered at a dose level of 10 µg/kg or 30 µg/kg.

24. The method of claim 1, further comprising administering one or more chemotherapeutic agents to the patient.

25. The method of claim 4, further comprising administering one or more chemotherapeutic agents to the patient.

26. The method of claim 7, further comprising administering one or more chemotherapeutic agents to the patient.

27. The method of claim 4, wherein the cancer is a hematologic cancer.

28. The method of claim 4, wherein the cancer is a solid tumor.

29. The method of claim 7, wherein the cancer is a hematologic cancer.

30. The method of claim 7, wherein the cancer is a solid tumor.

31. The method of claim 22, further comprising administering one or more chemotherapeutic agents to the patient.

32. The method of claim 31, wherein the one or more chemotherapeutic agents comprise gemcitabine, paclitaxel, or both.

33. A method of treating cancer, the method comprising administering a composition comprising an anti-CD40 antibody to a patient in need thereof,
    wherein the anti-CD40 antibody comprises a heavy chain variable region comprising amino acids 1-113 of SEQ ID NO:1 and a light chain variable region comprising amino acids 1-113 of SEQ ID NO:2, and a human constant region;
    wherein the constant region has an N-glycoside-linked sugar chain at residue N297 according to the EU index; and wherein less than 5% of N-glycoside-linked sugar chains in the composition comprise a fucose residue; and
    wherein the anti-CD40 antibody is administered at a dose level of 10 µg/kg (µg per kilogram of patient body weight).

34. The method of claim 33, wherein the anti-CD40 is administered at least once every three weeks.

35. The method of claim 34, wherein the anti-CD40 antibody is administered on day one of a three week cycle.

36. The method of claim 33, wherein the patient has a CD40 positive cancer.

37. The method of claim 33, wherein the patient has a CD40 negative cancer.

38. The method of claim 33, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

39. The method of claim 38, wherein the cancer is pancreatic cancer.

40. The method of claim 33, further comprising administering an anti-PD-1 antibody to the patient, wherein the anti-PD-1 antibody is nivolumab or pembrolizumab.

41. The method of claim 40, wherein the anti-PD-1 antibody is pembrolizumab.

42. The method of claim 33, further comprising administering one or more chemotherapeutic agents to the patient.

43. The method of claim 33, wherein the cancer is a hematologic cancer.

44. The method of claim 33, wherein the cancer is a solid tumor.

45. The method of claim 1, wherein the anti-CD40 antibody is administered at least once every three weeks.

46. The method of claim 13, wherein the cancer is melanoma.

47. The method of claim 13, wherein the cancer is non-small cell lung cancer.

48. The method of claim 13, wherein the cancer is head and neck cancer.

49. The method of claim 24, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

50. The method of claim 49, wherein the cancer is pancreatic cancer.

51. The method of claim 49, wherein the cancer is melanoma.

52. The method of claim 49, wherein the cancer is non-small cell lung cancer.

53. The method of claim 49, wherein the cancer is head and neck cancer.

54. The method of claim 45, wherein the anti-CD40 antibody is administered on day one of a three week cycle.

55. The method of claim 54, further comprising administering one or more chemotherapeutic agents to the patient.

56. The method of claim 55, wherein the one or more chemotherapeutic agents comprise gemcitabine, paclitaxel, or both.

57. The method of claim 1, wherein the anti-CD40 antibody is administered intravenously or subcutaneously to the patient.

58. The method of claim 4, wherein the patient has a CD40 positive cancer.

59. The method of claim 4, wherein the patient has a CD40 negative cancer.

60. The method of claim 4, wherein the dose level is 10 µg/kg or 30 µg/kg.

61. The method of claim 15, wherein the anti-CD40 antibody is administered intravenously or subcutaneously to the patient.

62. The method of claim 61, wherein the cancer is melanoma.

63. The method of claim 61, wherein the cancer is non-small cell lung cancer.

64. The method of claim 61, wherein the cancer is head and neck cancer.

65. The method of claim 16, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

66. The method of claim 65, wherein the cancer is pancreatic cancer.

67. The method of claim 65, wherein the cancer is melanoma.

68. The method of claim 65, wherein the cancer is non-small cell lung cancer.

69. The method of claim 65, wherein the cancer is head and neck cancer.

70. The method of claim 25, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

71. The method of claim 70, wherein the cancer is pancreatic cancer.

72. The method of claim 70, wherein the cancer is melanoma.

73. The method of claim 70, wherein the cancer is non-small cell lung cancer.

74. The method of claim 70, wherein the cancer is head and neck cancer.

75. The method of claim 70, wherein the anti-PD-1 antibody is pembrolizumab.

76. The method of claim 75, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

77. The method of claim 76, wherein the cancer is pancreatic cancer.

78. The method of claim 76, wherein the cancer is melanoma.

79. The method of claim 76, wherein the cancer is non-small cell lung cancer.

80. The method of claim 76, wherein the cancer is head and neck cancer.

81. The method of claim 25, wherein the anti-PD-1 antibody is pembrolizumab.

82. The method of claim 81, wherein the anti-CD40 antibody is administered intravenously or subcutaneously to the patient.

83. The method of claim 82, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

84. The method of claim 83, wherein the cancer is pancreatic cancer.

85. The method of claim 83, wherein the cancer is melanoma.

86. The method of claim 83, wherein the cancer is non-small cell lung cancer.

87. The method of claim 83, wherein the cancer is head and neck cancer.

88. The method of claim 4, wherein the anti-CD40 antibody is administered intravenously or subcutaneously to the patient.

89. The method of claim 18, wherein the cancer is melanoma.

90. The method of claim 18, wherein the cancer is non-small cell lung cancer.

91. The method of claim 18, wherein the cancer is head and neck cancer.

92. The method of claim 26, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

93. The method of claim 92, wherein the cancer is pancreatic cancer.

94. The method of claim 92, wherein the cancer is melanoma.

95. The method of claim 92, wherein the cancer is non-small cell lung cancer.

96. The method of claim 92, wherein the cancer is head and neck cancer.

97. The method of claim 7, wherein the anti-CD40 antibody is administered intravenously or subcutaneously to the patient.

98. The method of claim 97, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

99. The method of claim 98, wherein the cancer is pancreatic cancer.

100. The method of claim 98, wherein the cancer is melanoma.

101. The method of claim 98, wherein the cancer is non-small cell lung cancer.

102. The method of claim 98, wherein the cancer is head and neck cancer.

103. The method of claim 34, wherein the anti-CD40 antibody is administered intravenously or subcutaneously to the patient.

104. The method of claim 34, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

105. The method of claim 104, wherein the cancer is pancreatic cancer.

106. The method of claim 104, wherein the cancer is melanoma.

107. The method of claim 104, wherein the cancer is non-small cell lung cancer.

108. The method of claim 104, wherein the cancer is head and neck cancer.

109. The method of claim 35, wherein the anti-CD40 antibody is administered intravenously or subcutaneously to the patient.

110. The method of claim 35, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

111. The method of claim 110, wherein the cancer is pancreatic cancer.

112. The method of claim 110, wherein the cancer is melanoma.

113. The method of claim 110, wherein the cancer is non-small cell lung cancer.

114. The method of claim 110, wherein the cancer is head and neck cancer.

115. The method of claim 38, wherein the cancer is melanoma.

116. The method of claim 38, wherein the cancer is non-small cell lung cancer.

117. The method of claim 38, wherein the cancer is head and neck cancer.

118. The method of claim 40, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

119. The method of claim 118, wherein the cancer is melanoma.

120. The method of claim 118, wherein the cancer is non-small cell lung cancer.

121. The method of claim 118, wherein the cancer is head and neck cancer.

122. The method of claim 41, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

123. The method of claim 122, wherein the cancer is pancreatic cancer.

124. The method of claim 122, wherein the cancer is melanoma.

125. The method of claim 122, wherein the cancer is non-small cell lung cancer.

126. The method of claim 122, wherein the cancer is head and neck cancer.

127. The method of claim 42, wherein the anti-CD40 antibody is administered intravenously or subcutaneously to the patient.

128. The method of claim 42, further comprising administering an anti-PD-1 antibody to the patient, wherein the anti-PD-1 antibody is nivolumab or pembrolizumab.

129. The method of claim 128, wherein the anti-PD-1 antibody is pembrolizumab.

130. The method of claim 129, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

131. The method of claim 130, wherein the cancer is pancreatic cancer.

132. The method of claim 130, wherein the cancer is melanoma.

133. The method of claim 130, wherein the cancer is non-small cell lung cancer.

134. The method of claim 130, wherein the cancer is head and neck cancer.

135. The method of claim 42, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

136. The method of claim 135, wherein the cancer is pancreatic cancer.

137. The method of claim 136, wherein the one or more chemotherapeutic agents comprise gemcitabine, paclitaxel, or both.

138. The method of claim 135, wherein the cancer is melanoma.

139. The method of claim 135, wherein the cancer is non-small cell lung cancer.

140. The method of claim 135, wherein the cancer is head and neck cancer.

141. The method of claim 135, further comprising administering an anti-PD-1 antibody to the patient, wherein the anti-PD-1 antibody is nivolumab or pembrolizumab.

142. The method of claim 141, wherein the anti-PD-1 antibody is pembrolizumab.

143. The method of claim 142, wherein the cancer is selected from the group consisting of melanoma, breast cancer, metastatic breast cancer, lung cancer, non-small cell lung cancer, bladder cancer, pancreatic cancer, B-cell lymphoma, Hodgkin lymphoma, diffuse large cell B-cell lymphoma, follicular lymphoma, chronic lymphocytic leukemia, small cell lung cancer, ovarian cancer, kidney cancer, cervical cancer, head and neck cancer, prostate cancer, glioblastoma, non-Hodgkin lymphoma, hepatocellular carcinoma, and multiple myeloma.

144. The method of claim 143, wherein the cancer is pancreatic cancer.

145. The method of claim 143, wherein the cancer is melanoma.

146. The method of claim 143, wherein the cancer is non-small cell lung cancer.

147. The method of claim 143, wherein the cancer is head and neck cancer.

148. The method of claim 142, wherein the one or more chemotherapeutic agents comprise both gemcitabine and paclitaxel.

149. The method of claim 148, wherein the cancer is pancreatic cancer.

150. The method of claim 142, wherein the one or more chemotherapeutic agents consist of cisplatin and carboplatin.

151. The method of claim 150, wherein the cancer is pancreatic cancer.

152. The method of claim 33, wherein the anti-CD40 antibody is administered intravenously or subcutaneously to the patient.

153. The method of claim 52, wherein the one or more chemotherapeutic agents comprise cisplatin or carboplatin.

154. The method of claim 153, wherein the one or more chemotherapeutic agents further comprises gemcitabine.

155. The method of claim 73, wherein the one or more chemotherapeutic agents comprise cisplatin or carboplatin.

156. The method of claim 155, wherein the one or more chemotherapeutic agents further comprises gemcitabine.

157. The method of claim 95, wherein the one or more chemotherapeutic agents comprise cisplatin or carboplatin.

158. The method of claim 157, wherein the one or more chemotherapeutic agents further comprises gemcitabine.

159. The method of claim 139, wherein the one or more chemotherapeutic agents comprise cisplatin or carboplatin.

160. The method of claim 159, wherein the one or more chemotherapeutic agents further comprises gemcitabine.

161. The method of claim 50, wherein the one or more chemotherapeutic agents comprise gemcitabine, paclitaxel, or both.

162. The method of claim 61, wherein the cancer is pancreatic cancer.

163. The method of claim 71, wherein the one or more chemotherapeutic agents comprise gemcitabine, paclitaxel, or both.

164. The method of claim 93, wherein the one or more chemotherapeutic agents comprise gemcitabine, paclitaxel, or both.

165. The method of claim 118, wherein the cancer is pancreatic cancer.

166. The method of claim 137, wherein the anti-CD40 antibody is administered intravenously or subcutaneously to the patient.

167. The method of claim 1, wherein the anti-CD40 antibody comprises a heavy chain comprising the amino acid sequence of SEQ ID NO: 1 and a light chain comprising the amino acid sequence of SEQ ID NO: 2.

168. The method of claim 4, wherein the anti-CD40 antibody comprises a heavy chain comprising the amino acid sequence of SEQ ID NO: 1 and a light chain comprising the amino acid sequence of SEQ ID NO: 2.

169. The method of claim 7, wherein the anti-CD40 antibody comprises a heavy chain comprising the amino acid sequence of SEQ ID NO: 1 and a light chain comprising the amino acid sequence of SEQ ID NO: 2.

170. The method of claim 33, wherein the anti-CD40 antibody comprises a heavy chain comprising the amino acid sequence of SEQ ID NO: 1 and a light chain comprising the amino acid sequence of SEQ ID NO: 2.

* * * * *